(12) United States Patent
Acosta et al.

(10) Patent No.: US 7,787,924 B2
(45) Date of Patent: *Aug. 31, 2010

(54) COMPACT APPARATUS FOR NONINVASIVE MEASUREMENT OF GLUCOSE THROUGH NEAR-INFRARED SPECTROSCOPY

(75) Inventors: George M. Acosta, Phoenix, AZ (US); James R. Henderson, Phoenix, AZ (US); N. Alan Abul Haj, Mesa, AZ (US); Timothy L. Ruchti, Gilbert, AZ (US); Stephen L. Monfre, Gilbert, AZ (US); Thomas B. Blank, Chandler, AZ (US); Kevin H. Hazen, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 1276 days.

This patent is subject to a terminal disclaimer.

(21) Appl. No.: 11/324,876

(22) Filed: Jan. 3, 2006

(65) Prior Publication Data
US 2006/0173254 A1 Aug. 3, 2006

Related U.S. Application Data

(63) Continuation of application No. 10/472,856, filed as application No. PCT/US03/07065 on Mar. 7, 2003, now Pat. No. 7,133,710.

(60) Provisional application No. 60/362,885, filed on Mar. 8, 2002, provisional application No. 60/362,899, filed on Mar. 8, 2002, provisional application No. 60/448,840, filed on Feb. 19, 2003.

(51) Int. Cl.
*A61B 5/1455* (2006.01)

(52) U.S. Cl. .................... 600/316; 600/344
(58) Field of Classification Search ........... 600/310, 600/316, 322, 344
See application file for complete search history.

(56) References Cited

U.S. PATENT DOCUMENTS

| 4,033,054 A | 7/1977 | Fukuoka |
|---|---|---|
| 4,213,462 A | 7/1980 | Sato |
| 4,272,040 A | 6/1981 | Bastian et al. |

(Continued)

FOREIGN PATENT DOCUMENTS

CN 1214768 4/1999

(Continued)

OTHER PUBLICATIONS

Diabetes Statistics. Bethesda, MD: National Institute of Health, Publication No. 98-3926, Nov. 1997.

(Continued)

*Primary Examiner*—Eric F Winakur
(74) *Attorney, Agent, or Firm*—Michael A. Glenn; Glenn Patent Group

(57) ABSTRACT

The invention involves the monitoring of a biological parameter through a compact analyzer. The preferred apparatus is a spectrometer based system that is attached continuously or semi-continuously to a human subject and collects spectral measurements that are used to determine a biological parameter in the sampled tissue. The preferred target analyte is glucose. The preferred analyzer is a near-IR based glucose analyzer for determining the glucose concentration in the body.

19 Claims, 6 Drawing Sheets

U.S. PATENT DOCUMENTS

| | | | |
|---|---|---|---|
| 4,321,930 A | 3/1982 | Jobsis | |
| 4,548,505 A | 10/1985 | Ono | |
| 4,674,338 A | 6/1987 | Carpenter | |
| 4,685,464 A | 8/1987 | Goldberger et al. | |
| 4,798,955 A | 1/1989 | Rosenthal | |
| 4,830,014 A | 5/1989 | Goodman et al. | |
| 4,866,644 A | 9/1989 | Shenk et al. | 364/571.02 |
| 4,882,492 A | 11/1989 | Schlager | 250/346 |
| 5,007,423 A | 4/1991 | Branstetter et al. | |
| 5,068,536 A | 11/1991 | Rosenthal | |
| 5,070,874 A | 12/1991 | Barnes et al. | |
| 5,131,391 A | 7/1992 | Sakai et al. | |
| 5,170,786 A | 12/1992 | Thomas | |
| 5,285,783 A | 2/1994 | Secker | |
| 5,299,570 A | 4/1994 | Hatschek | |
| 5,348,003 A | 9/1994 | Caro | |
| 5,361,758 A | 11/1994 | Hall et al. | |
| 5,398,681 A | 3/1995 | Kupershmidt | |
| 5,448,662 A | 9/1995 | Kittell | |
| 5,492,118 A | 2/1996 | Gratton | |
| 5,506,482 A | 4/1996 | Teramatsu | |
| 5,507,288 A | 4/1996 | Bocker et al. | |
| 5,517,301 A | 5/1996 | Dave | |
| 5,548,674 A | 8/1996 | Rondeau | |
| 5,574,855 A | 11/1996 | Rosich et al. | |
| 5,596,987 A | 1/1997 | Chance | |
| 5,619,195 A | 4/1997 | Allen | |
| 5,632,273 A | 5/1997 | Suzuki | |
| 5,636,634 A | 6/1997 | Kordis | |
| 5,655,530 A | 8/1997 | Messerschmidt | |
| 5,661,843 A | 8/1997 | Rickenbach | |
| 5,671,317 A | 9/1997 | Weishaupt | |
| 5,687,717 A | 11/1997 | Halpern et al. | |
| 5,725,480 A | 3/1998 | Ooste | |
| 5,730,140 A | 3/1998 | Fitch | |
| 5,747,806 A | 5/1998 | Khalil et al. | 250/339.12 |
| 5,750,994 A | 5/1998 | Schlager | 250/339.11 |
| 5,769,076 A | 6/1998 | Maekawa | |
| 5,770,454 A | 6/1998 | Essenpreis et al. | |
| 5,823,951 A | 10/1998 | Messerschmidt | 600/322 |
| 5,825,488 A | 10/1998 | Kohl et al. | |
| 5,830,132 A | 11/1998 | Robinson | |
| 5,869,075 A | 2/1999 | Krzysik | |
| 5,877,664 A | 3/1999 | Jackson, Jr. | |
| 5,879,373 A | 3/1999 | Roper et al. | |
| 5,891,021 A | 4/1999 | Dillon | |
| 5,912,656 A | 6/1999 | Tham et al. | |
| 5,935,062 A | 8/1999 | Messerschmidt et al. | 600/322 |
| 5,945,676 A | 8/1999 | Khalil et al. | 250/399.12 |
| 5,956,150 A | 9/1999 | Kanne | |
| 5,978,691 A | 11/1999 | Mills | |
| 6,014,756 A | 1/2000 | Dottling | |
| 6,016,435 A | 1/2000 | Maruo et al. | |
| 6,040,578 A | 3/2000 | Malin et al. | 250/339.12 |
| 6,045,511 A | 4/2000 | Ott | |
| 6,067,463 A | 5/2000 | Jeng et al. | |
| 6,088,605 A | 7/2000 | Griffith et al. | |
| 6,093,156 A | 7/2000 | Cunningham et al. | |
| 6,095,974 A | 8/2000 | Shemwell et al. | |
| 6,115,673 A | 9/2000 | Malin et al. | 702/23 |
| 6,144,868 A | 11/2000 | Parker | |
| 6,147,749 A | 11/2000 | Kubo et al. | |
| 6,152,876 A | 11/2000 | Robinson et al. | 600/322 |
| 6,157,041 A | 12/2000 | Thomas et al. | |
| 6,180,416 B1 | 1/2001 | Kurnik et al. | 436/518 |
| 6,217,506 B1 | 4/2001 | Phillips et al. | |
| 6,230,034 B1 | 5/2001 | Messerschmidt et al. | 600/322 |
| 6,233,471 B1 | 5/2001 | Berner et al. | 600/345 |
| 6,236,047 B1 | 5/2001 | Malin et al. | 250/339.12 |
| 6,240,306 B1 | 5/2001 | Rohrscheib et al. | 600/316 |
| 6,253,097 B1 | 6/2001 | Aronow et al. | |
| 6,272,364 B1 | 8/2001 | Kurnik | 600/345 |
| 6,280,381 B1 | 8/2001 | Malin et al. | 600/322 |
| 6,289,230 B1 | 9/2001 | Chaiken et al. | |
| 6,304,766 B1 | 10/2001 | Colvin, Jr. | 600/317 |
| 6,326,160 B1 | 12/2001 | Dunn et al. | 435/14 |
| 6,330,464 B1 | 12/2001 | Colvin, Jr. et al. | 600/316 |
| 6,334,360 B1 | 1/2002 | Chen | 73/304 |
| 6,381,489 B1 | 4/2002 | Ashibe | |
| 6,400,974 B1 | 6/2002 | Lesho | 600/347 |
| 6,405,065 B1 | 6/2002 | Malin et al. | 600/310 |
| 6,411,373 B1 | 6/2002 | Garside et al. | 356/39 |
| 6,411,838 B1 | 6/2002 | Nordstrom et al. | |
| 6,415,167 B1 | 7/2002 | Blank et al. | 600/344 |
| 6,421,549 B1 | 7/2002 | Jacques | |
| 6,441,388 B1 | 8/2002 | Thomas | |
| 6,442,408 B1 | 8/2002 | Wenzel et al. | 600/310 |
| 6,449,500 B1 | 9/2002 | Asai et al. | |
| 6,456,870 B1 | 9/2002 | Rennert et al. | 600/475 |
| 6,475,800 B1 | 11/2002 | Hazen et al. | 436/8 |
| 6,487,429 B2 | 11/2002 | Hockersmith et al. | 600/316 |
| 6,493,566 B1 | 12/2002 | Ruchti et al. | 600/310 |
| 6,501,982 B1 | 12/2002 | Ruchti et al. | 600/473 |
| 6,507,687 B1 | 1/2003 | Juskaitis et al. | |
| 6,512,937 B2 | 1/2003 | Blank et al. | 600/322 |
| 6,512,982 B2 | 1/2003 | Yang et al. | |
| 6,528,809 B1 | 3/2003 | Thomas | |
| 6,546,269 B1 | 4/2003 | Kurnik | |
| 6,558,320 B1 | 5/2003 | Causey et al. | |
| 6,574,490 B2 | 6/2003 | Abbink et al. | |
| 6,585,370 B2 | 7/2003 | Zelman | |
| 6,631,282 B2 | 10/2003 | Rule et al. | |
| 6,641,533 B2 | 11/2003 | Causey, III et al. | |
| 6,690,958 B1 | 2/2004 | Walker et al. | |
| 6,788,965 B2 | 9/2004 | Ruchti | |
| 6,839,583 B1 | 1/2005 | Lewandowski et al. | |
| 6,920,345 B2 | 7/2005 | Al-Ali et al. | |
| 6,927,843 B2 | 8/2005 | Dick | |
| 7,133,710 B2 | 11/2006 | Acosta et al. | |
| 7,178,063 B1 | 2/2007 | Smith | |
| 7,409,330 B2 | 8/2008 | Kumamoto | |
| 2002/0026106 A1 | 2/2002 | Khalil et al. | |
| 2002/0058864 A1 | 5/2002 | Mansfield | |
| 2002/0087949 A1 | 7/2002 | Golender et al. | |
| 2003/0040663 A1 | 2/2003 | Rule | |
| 2003/0109775 A1 | 6/2003 | O'Neil et al. | |
| 2003/0156270 A1 | 8/2003 | Hunter | |
| 2003/0208113 A1 | 11/2003 | Mault et al. | |
| 2003/0216627 A1 | 11/2003 | Lorenz | |
| 2003/0216630 A1 | 11/2003 | Jersey-Willuhn et al. | |
| 2004/0068163 A1 | 4/2004 | Ruchti | |
| 2004/0077937 A1 | 4/2004 | Yarden | |
| 2004/0127777 A1 | 7/2004 | Ruchti | |
| 2004/0163032 A1 | 8/2004 | Guo | |
| 2004/0167473 A1 | 8/2004 | Moenning | |
| 2004/0267485 A1 | 12/2004 | Penov et al. | |
| 2005/0007125 A1 | 1/2005 | Heger | |
| 2005/0034102 A1 | 2/2005 | Peck | |
| 2005/0054908 A1 | 3/2005 | Blank et al. | |
| 2005/0187439 A1 | 8/2005 | Blank et al. | |
| 2005/0267342 A1 | 12/2005 | Blank et al. | |
| 2006/0200017 A1 | 9/2006 | Monfre et al. | |
| 2006/0211931 A1 | 9/2006 | Blank et al. | |
| 2006/0217602 A1 | 9/2006 | Abul-Haj et al. | |
| 2008/0009835 A1 | 1/2008 | Kriesel et al. | |
| 2008/0033275 A1 | 2/2008 | Blank et al. | |
| 2009/0062635 A1 | 3/2009 | Brauker et al. | |

FOREIGN PATENT DOCUMENTS

| | | |
|---|---|---|
| DE | 2640987 | 3/1978 |
| EP | 1254631 | 11/2002 |
| JP | 04-215742 | 8/1992 |
| JP | 05-317295 | 12/1993 |

| | | |
|---|---|---|
| JP | 08-215180 | 8/1996 |
| JP | 2001-037741 | 2/2001 |
| JP | 2001-299727 | 10/2001 |
| JP | 2002535023 | 10/2002 |
| WO | WO 96/28084 | 9/1996 |
| WO | WO 97/05819 | 2/1997 |
| WO | WO 97/28437 | 8/1997 |
| WO | WO 00/22982 | 4/2000 |
| WO | WO 00/42907 | 7/2000 |
| WO | WO 00/74562 | 12/2000 |
| WO | WO 00/76575 A3 | 12/2000 |
| WO | WO 01/31304 | 5/2001 |
| WO | WO 01/58355 | 8/2001 |
| WO | WO 01/72222 | 10/2001 |
| WO | WO 01/82794 | 11/2001 |
| WO | WO 02/65090 | 8/2002 |
| WO | WO03/105664 | 12/2003 |

OTHER PUBLICATIONS

The Diabetes Control and Complications Trial Research Group. "The effect of intensive treatment of diabetes on the development and progression of long-term complications in insulin-dependent diabetes mellitus." N Eng J of Med 1993;329:977-86.

U.K. Prospective Diabetes Study (UKPDS) Group, "Intensive blood-glucose control with sulphonylureas or insulin compared with conventional treatment and risk of complications in patients with type 2 diabetes," Lancet, vol. 352, pp. 837-853, 1998.

Ohkubo, Y., H. Kishikawa, E. Araki, T. Miyata, S. Isami, S. Motoyoshi, Y. Kojima, N. Furuyoshi, and M. Shichizi, "Intensive insulin therapy prevents the progression of diabetic microvascular complications in Japanese patients with non-insulin-dependent diabetes mellitus: a randomized prospective 6-year study," Diabetes Res Clin Pract, vol. 28, pp. 103-117, 1995.

Savitzky, A. and M. J. E. Golay. "Smoothing and Differentiation of Data by Simplified Least Squares Procedures," Anal. Chem., vol. 36, No. 8, pp. 1627-1639, 1964.

Hazen, Kevin H. "Glucose Determination in Biological Matrices Using Near-Infrared Spectr Sage, Burton H. "FDA Panel Approves Cygnus's Noninvasive GlucoWatch™", Diabetes Technology & Therapeutics, 2, 2000, 115-116.oscopy", doctoral dissertation, University of Iowa, 1995.

Tamada, J.A., S. Garg, L. Jovanovic, K.R. Pitzer, S. Fermi, R.O. Potts, "Noninvasive Glucose Monitoring Comprehensive Clinical Results," JAMA, vol. 282, No. 19, pp. 1839-1844, Nov. 17, 1999.

"GlucoWatch Automatic Glucose Biographer and AutoSensors", Cygnus Inc., Document #1992-00, Rev. Mar. 2001.

Trajanowski, Zlatko; Brunner, Gernot A.; Schaupp, Lucas; Ellmerer, Martin; Wach, Paul; Pieber, Thomas R,; Kotanko, Peter; Skrabai, Falko "Open-Flow Microperfusion of Subcutaneous Adipose Tissue for ON-Line Continuous Ex Vivo Measurement of Glucose Concentration", Diabetes Care, 20, 1997, 1114-1120.

Trajanowski, Zlatko; Wach, Paul; Gfrerer, Robert "Portable Device for Continuous Fractionated Blood Sampling and Continuous ex vivo Blood Glucose Monitoring", Biosensors and Bioelectronics, 11, 1996, 479-487.

Gross, Todd M.; Bode, Bruce W.; Einhorn, Daniel; Kayne, David M.; Reed, John H.; White, Neil H.; Mastrototaro, John J. "Performance Evaluation of the MiniMed Continuous Glucose Monitoring System During Patient Home Use", Diabetes Technology & Therapeutics, 2, 2000, 49-56.

Rebrin, Kerstin; Steil, Gary M.; Antwerp, William P. Van; Mastrototaro, John J. "Subcutaneous Glucose Predicts Plasma Glucose Independent of Insulin: Implications for Continuous Monitoring", Am., J. Physiol., 277, 1999, E561-E571, 0193-1849-99, The American Physiological Society, 1999.

Geladi, P., D. McDougall and H. Martens. "Linearization and Scatter-Correction for Near-Infrared Reflectance Spectra of Meat," Applied Spectroscopy, vol. 39, pp. 491-500, 1985.

R.J. Barnes, M.S. Dhanoa, and S. Lister, Standard Normal Variate Transformation and De-trending of Near-Infrared Diffuse Reflectance Spectra, Applied Spectroscopy, 43, pp. 772-777, 1989.

T. Isaksson and B. R. Kowalski, "Piece-Wise Multiplicative Scatter Correction Applied to Near-Infrared Diffuse Transmittance Data From Meat Products", Applied Spectroscopy, 47, pp. 702-709, 1993.

H. Martens and E. Stark, "Extended multiplicative signal correction and spectral interference subtraction: new preprocessing methods for near infrared spectroscopy", J. Pharm Biomed Anal, 9, pp. 625-635, 1991.

T. Isaksson, Z. Wang, and B. R. Kowalski, Optimised scaling (OS-2) regression applied to near infrared . . . food products, J. Near Infrared Spectroscopy, 1, pp. 85-97, 1993.

Sum, S.T., "Spectral Signal Correction for Multivariate Calibration," Doctoral Disseration, University of Delaware, Summer 1998.

Sum, S.T. and S.D. Brown, "Standardization of Fiber-Optic Probes for Near-Infrared Multivariate Calibrations," Applied Spectroscopy, vol. 52, No. 6, pp. 869-877, 1998.

T. B. Blank, S.T. Sum, S.D. Brown and S.L. Monfre, "Transfer of near-infrared multivariate calibrations without standards," Analytical Chemistry, 68, pp. 2987-2995, 1996.

Massart, D.L., B.G.M. Vandeginste, S.N. Deming, Y. Michotte and L. Kaufman, Chemometrics: a textbook, New York: Elsevier Science Publishing Company, Inc., 1990.

Oppenheim, Alan V. and R. W. Schafer, Digital Signal Processing, Englewood Cliffs, NJ: Prentice Hall, 1975, pp. 195-271.

Otto, M., Statistics and Computer Application in Analytical Chemistry; Chemometrics, Weinheim: Wiley-VCH, 1999.

Beebe, K.R., R.J. Pell and M.B. Seasholtz, Chemometrics A Practical Guide, New York: John Wiley & Sons, Inc., 1998.

M.A. Sharaf, D.L. Illman and B.R. Kowalski, Chemometrics, New York: John Wiley & Sons, Inc., 1996.

Webster's II New Riverside University Dictionary: The Riverside Publishing Company, 1994, p. 1000.

Barnes, R.J. et al., "Standard Normal Variate Transformation and De-trending of Near-Infrared Diffuse Reflectance Spectra", Applied Spectroscopy, vol. 43, No. 5, pp. 772-777, 1989.

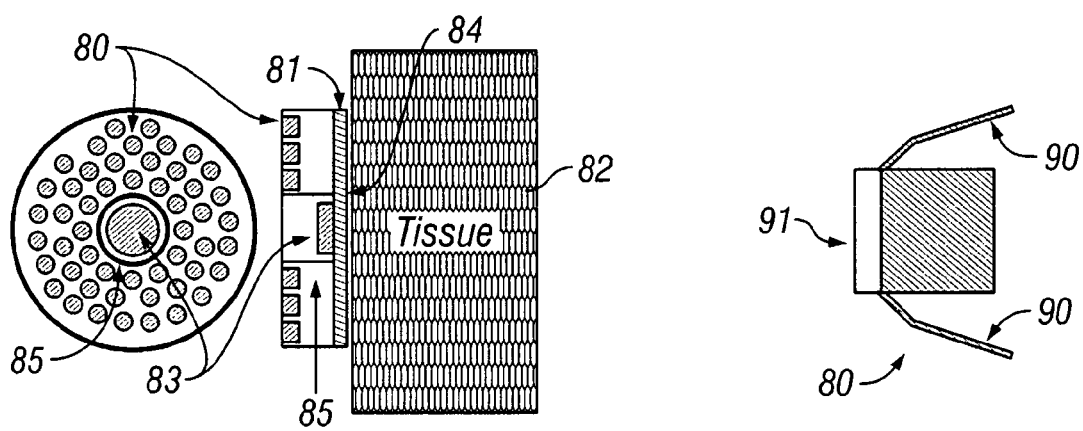
FIG. 8
FIG. 9
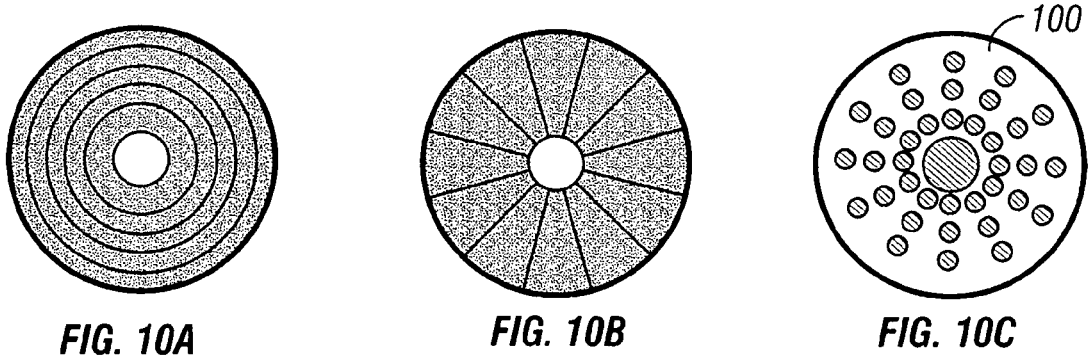
FIG. 10A  FIG. 10B  FIG. 10C

COMPACT APPARATUS FOR NONINVASIVE MEASUREMENT OF GLUCOSE THROUGH NEAR-INFRARED SPECTROSCOPY

CROSS REFERENCE TO RELATED APPLICATIONS

This application is a continuation of U.S. patent application Ser. No. 10/472,856 filed Mar. 3, 2003, now U.S. Pat. No. 7,133,710 which claims:
priority to PCT application no. PCT/US03/07065 filed Mar. 7, 2003, which claims benefit of U.S. provisional patent application No. 60/362,885, filed on Mar. 8, 2002;
benefit of U.S. provisional patent application No. 60/362,899, filed on Mar. 8, 2002; and
benefit of U.S. provisional patent application No. 60/448,840 filed on Feb. 19, 2003.

BACKGROUND OF THE INVENTION

1. Field of the Invention

This invention relates generally to the noninvasive measurement of biological parameters through near-infrared spectroscopy. In particular, an apparatus and a method are disclosed for noninvasively, and continuously or semi-continuously, monitoring a biological parameter, such as glucose in tissue.

2. Discussion of the Prior Art

Diabetes

Diabetes is a chronic disease that results in improper production and use of insulin, a hormone that facilitates glucose uptake into cells. Diabetes can be broadly categorized into four forms: diabetes, impaired glucose tolerance, normal physiology, and hyperinsulinemia (hypoglycemia). While a precise cause of diabetes is unknown, genetic factors, environmental factors, and obesity appear to play roles.

Diabetics have increased risk in three broad categories: cardiovascular heart disease, retinopathy, and neuropathy. Diabetics may have one or more of the following complications: heart disease and stroke, high blood pressure, kidney disease, neuropathy (nerve disease and amputations), retinopathy, diabetic ketoacidosis, skin conditions, gum disease, impotence, and fetal complications. Diabetes is a leading cause of death and disability worldwide.

Diabetes Prevalence and Trends

Diabetes is a common and growing disease. The World Health Organization (WHO) estimates that diabetes currently afflicts one hundred fifty-four million people worldwide. Fifty-four million diabetics live in developed countries. The WHO estimates that the number of people with diabetes will grow to three hundred million by the year 2025. In the United States, 15.7 million people or 5.9% of the population are estimated to have diabetes. Within the United States, the prevalence of adults diagnosed with diabetes increased by six percent in 1999 and rose by thirty-three percent between 1990 and 1998. This corresponds to approximately eight hundred thousand new cases every year in America. The estimated total cost to the United States economy alone exceeds $90 billion per year (Diabetes Statistics. Bethesda, MD: National Institute of Health, Publication No. 98-3926, November 1997).

Long-term clinical studies show that the onset of diabetes related complications can be significantly reduced through proper control of blood glucose concentrations (The Diabetes Control and Complications Trial Research Group. The effect of intensive treatment of diabetes on the development and progression of long-term complications in insulin-dependent diabetes mellitus. N Eng J of Med 1993;329:977-86; U.K. Prospective Diabetes Study (UKPDS) Group, "Intensive blood-glucose control with sulphonylureas or insulin compared with conventional treatment and risk of complications in patients with type 2 diabetes," *Lancet, vol.* 352, pp. 837-853, 1998; Ohkubo, Y., H. Kishikawa, E. Araki, T. Miyata, S. Isami, S. Motoyoshi, Y. Kojima, N. Furuyoshi, and M. Shichizi, "Intensive insulin therapy prevents the progression of diabetic microvascular complications in Japanese patients with non-insulin-dependent diabetes mellitus: a randomized prospective 6-year study," *Diabetes Res Clin Pract*, vol. 28, pp. 103-117, 1995). A vital element of diabetes management is the self-monitoring of blood glucose levels by diabetics in the home environment. However, current monitoring techniques discourage regular use due to the inconvenient and painful nature of drawing blood through the skin prior to analysis (The Diabetes Control and Complication Trial Research Group, "The effect of intensive treatment of diabetes on the development and progression of long-term complications of insulin-dependent diabetes mellitus", *N. Engl. J. Med.*, 329, 1993, 997-1036). Unfortunately, recent reports indicate that even periodic measurement of glucose by individuals with diabetes, (e.g. seven times per day) is insufficient to detect important glucose fluctuations and properly manage the disease. In addition, nocturnal monitoring of glucose levels is of significant value but is difficult to perform due to the state of existing technology. Therefore, a device that provides noninvasive, automatic, and nearly continuous measurements of glucose levels would be of substantial value to people with diabetes. Implantable glucose analyzers eventually coupled to an insulin delivery system providing an artificial pancreas are also being pursued.

Description of Related Technology

Common technologies are used to analyze the blood glucose concentration of samples collected by venous draw and with capillary stick approaches. Glucose analysis includes techniques such as colorimetric and enzymatic glucose analysis. Many of the invasive, traditional invasive, alternative invasive, and minimally invasive glucose analyzers use these technologies. The most common enzymatic based glucose analyzers use glucose oxidase, which catalyzes the reaction of glucose with oxygen to form gluconolactone and hydrogen peroxide, equation 1. Glucose determination may be achieved by techniques based upon depletion of oxygen in the sample, through the changes in sample pH, or via the formation of hydrogen peroxide. A number of colorimetric and electro-enzymatic techniques further use the reaction products as a starting reagent. For example, hydrogen peroxide reacts in the presence of platinum to form the hydrogen ion, oxygen, and current any of which may be used to determine the glucose concentration, equation 2.

$$\text{glucose} + O_2 \rightarrow \text{gluconolactone} + H_2O_2 \quad \text{eq. 1}$$

$$H_2O_2 \rightarrow 2H^+ + O_2 + 2e^- \quad \text{eq. 2}$$

Due to the wide and somewhat loose terminology in the field, the terms traditional invasive, alternative invasive, noninvasive, and implantable are here outlined:

Traditional Invasive Glucose Determination

There are three major categories of traditional (classic) invasive glucose determinations. The first two methodologies use blood drawn with a needle from an artery or vein, respectively. The third group consists of capillary blood obtained via lancet from the fingertip or toes. Over the past two decades, this last method has become the most common method for self-monitoring of blood glucose at home, at work, or in public settings.

Alternative Invasive Glucose Determination

There are several alternative invasive methods of determining glucose concentrations.

A first group of alternative invasive glucose analyzers have a number of similarities to traditional invasive glucose analyzers. One similarity is that blood samples are acquired with a lancet. Obviously, this form of alternative invasive glucose determination may not be used to collect venous or arterial blood for analysis, but may be used to collect capillary blood samples. A second similarity is that the blood sample is analyzed using chemical analyses that are similar to the calorimetric and enzymatic analyses describe above. The primary difference is that in an alternative invasive glucose determination the blood sample is not collected from the fingertip or toes. For example, according to package labeling the TheraSense® FreeStyle Meter™ may be used to collect and analyze blood from the forearm. This is an alternative invasive glucose determination due to the location of the lancet draw.

In this first group of alternative invasive methods based upon blood draws with a lancet, a primary difference between the alternative invasive and traditional invasive glucose determination is the location of blood acquisition from the body. Additional differences include factors such as the gauge of the lancet, the depth of penetration of the lancet, timing issues, the volume of blood acquired, and environmental factors such as the partial pressure of oxygen, altitude, and temperature. This form of alternative invasive glucose determination includes samples collected from the palmar region, base of thumb, forearm, upper arm, head, earlobe, torso, abdominal region, thigh, calf, and plantar region.

A second group of alternative invasive glucose analyzers are distinguished by their mode of sample acquisition. This group of glucose analyzers has a common characteristic of acquiring a biological sample from the body or modifying the surface of the skin to gather a sample without use of a lancet for subsequent analysis. For example, a laser poration based glucose analyzer would use a burst or stream of photons to create a small hole in the surface of the skin. A sample of basically interstitial fluid would collect in the resulting hole. Subsequent analysis of the sample for glucose would constitute an alternative invasive glucose analysis whether or not the sample was actually removed from the created hole. A second common characteristic is that a device and algorithm are used to determine glucose from the sample.

A number of methodologies exist for the collection of the sample for alternative invasive measurements including laser poration, applied current, and suction. The most common are summarized here:

A. Laser poration: In these systems, photons of one or more wavelengths are applied to skin creating a small hole in the skin barrier. This allows small volumes of interstitial fluid to become available to a number of sampling techniques.

B. Applied current: In these systems, a small electrical current is applied to the skin allowing interstitial fluid to permeate through the skin.

C. Suction: In these systems, a partial vacuum is applied to a local area on the surface of the skin. Interstitial fluid permeates the skin and is collected.

For example, a device that acquires a sample via iontophoresis, such as Cygnus'® GlucoWatch™, is an alternative invasive technique.

In all of these techniques, the analyzed sample is interstitial fluid. However, some of the techniques can be applied to the skin in a fashion that draws blood. Herein, the term alternative invasive includes techniques that analyze biosamples such as interstitial fluid, whole blood, mixtures of interstitial fluid and whole blood, and selectively sampled interstitial fluid. An example of selectively sampled interstitial fluid is collected fluid in which large or less mobile constituents are not fully represented in the resulting sample. For this group of alternative invasive glucose analyzers sampling sites include: the hand, fingertips, palmar region, base of thumb, forearm, upper arm, head, earlobe, eye, chest, torso, abdominal region, thigh, calf, foot, plantar region, and toes. In this document, any technique that draws biosamples from the skin without the use of a lancet on the fingertip or toes is referred to as an alternative invasive technique.

In addition, it is recognized that the alternative invasive systems each have different sampling approaches that lead to different subsets of the interstitial fluid being collected. For example, large proteins might lag behind in the skin while smaller, more diffusive, elements may be preferentially sampled. This leads to samples being collected with varying analyte and interferent concentrations. Another example is that a mixture of whole blood and interstitial fluid may be collected. Another example is that a laser poration method can result in blood droplets. These techniques may be used in combination. For example the Soft-Tact, SoftSense in Europe, applies a suction to the skin followed by a lancet stick. Despite the differences in sampling, these techniques are referred to as alternative invasive techniques sampling interstitial fluid.

Sometimes, the literature refers to the alternative invasive technique as an alternative site glucose determination or as a minimally invasive technique. The minimally invasive nomenclature derives from the method by which the sample is collected. In this document, the alternative site glucose determinations that draw blood or interstitial fluid, even ¼ microliter, are considered to be alternative invasive glucose determination techniques as defined above. Examples of alternative invasive techniques include the TheraSense® FreeStyle™ when not sampling fingertips or toes, the Cygnus® GlucoWatch™, the One Touch® Ultra™, and equivalent technologies.

Biosamples collected with alternative invasive techniques are analyzed via a large range of technologies. The most common of these technologies are summarized below:

A. Conventional: With some modification, the interstitial fluid samples may be analyzed by most of the technologies used to determine glucose concentrations in serum, plasma, or whole blood. These include electrochemical, electroenzymatic, and calorimetric approaches. For example, the enzymatic and colorimetric approaches described above may also be used to determine the glucose concentration in interstitial fluid samples.

B. Spectrophotometric: A number of approaches, for determining the glucose concentration in biosamples, have been developed that are based upon spectrophotometric technologies. These techniques include: Raman and fluorescence, as well as techniques using light from the ultraviolet through the infrared [ultraviolet (200 to 400 nm), visible (400 to 700 nm), near-IR (700 to 2500 nm or 14,286 to 4000 $cm^{-1}$), and infrared (2500 to 14,285 nm or 4000 to 700 $cm^{-1}$)].

In this document, an invasive glucose analyzer is the genus of both the traditional invasive glucose analyzer species and the alternative invasive glucose analyzer species.

Noninvasive Glucose Determination

There exist a number of noninvasive approaches for glucose determination. These approaches vary widely, but have at least two common steps. First, an apparatus is used to acquire a reading from the body without obtaining a biological sample. Second, an algorithm is used to convert this reading into a glucose determination.

One species of noninvasive glucose analyzers are those based upon the collection and analysis of spectra. Typically, a noninvasive apparatus uses some form of spectroscopy to acquire the signal or spectrum from the body. Used spectroscopic techniques include but are not limited to Raman, fluorescence, as well as techniques using light from ultraviolet through the infrared [ultraviolet (200 to 400 nm), visible (400 to 700 nm), near-IR (700 to 2500 nm or 14,286 to 4000 $cm^{-1}$), and infrared (2500 to 14,285 nm or 4000 to 700 $cm^{-1}$)]. A particular range for noninvasive glucose determination in diffuse reflectance mode is about 1100 to 2500 nm or ranges therein (Hazen, Kevin H. "Glucose Determination in Biological Matrices Using Near-infrared Spectroscopy", doctoral dissertation, University of Iowa, 1995). It is important to note, that these techniques are distinct from the traditionally invasive and alternative invasive techniques listed above in that the sample analyzed is a portion of the human body in-situ, not a biological sample acquired from the human body.

Typically, three modes are used to collect noninvasive scans: transmittance, transflectance, and/or diffuse reflectance. For example the light, spectrum, or signal collected may be light transmitting through a region of the body, diffusely transmitting, diffusely reflected, or transflected. Transflected here refers to collection of the signal not at the incident point or area (diffuse reflectance), and not at the opposite side of the sample (transmittance), but rather at some point or region of the body between the transmitted and diffuse reflectance collection area. For example, transflected light enters the fingertip or forearm in one region and exits in another region. When using the near-IR, the transflected radiation typically radially disperses 0.2 to 5 mm or more away from the incident photons depending on the wavelength used. For example, light that is strongly absorbed by the body such as light near the water absorbance maxima at 1450 or 1950 nm must be collected after a small radial divergence in order to be detected and light that is less absorbed such as light near water absorbance minima at 1300, 1600, or 2250 nm may be collected at greater radial or transflected distances from the incident photons.

Noninvasive techniques are not limited to the fingertip. Other regions or volumes of the body subjected to noninvasive measurements are: a hand, finger, palmar region, base of thumb, forearm, volar aspect of the forearm, dorsal aspect of the forearm, upper arm, head, earlobe, eye, tongue, chest, torso, abdominal region, thigh, calf, foot, plantar region, and toe. It is important to note that noninvasive techniques do not have to be based upon spectroscopy. For example, a bioimpedence meter would be a noninvasive device. In this document, any device that reads glucose from the body without penetrating the skin and collecting a biological sample is referred to as a noninvasive glucose analyzer. For the purposes of this document, X-rays and MRI's are not considered to be defined in the realm of noninvasive technologies.

Implantable Sensor for Glucose Determination

There exist a number of approaches for implanting a glucose sensor into the body for glucose determination. These implantables may be used to collect a sample for further analysis or may acquire a reading of the sample directly or based upon direct reactions occurring with glucose. Two categories of implantable glucose analyzers exist: short-term and long-term.

In this document, a device or a collection apparatus is referred to as a short-term implantable (as opposed to a long-term implantable) if part of the device penetrates the skin for a period of greater than three hours and less than one month. For example, a wick placed subcutaneously to collect a sample overnight that is removed and analyzed for glucose content representative of the interstitial fluid glucose concentration is referred to as a short term implantable. Similarly, a biosensor or electrode placed under the skin for a period of greater than three hours that reads directly or based upon direct reactions occurring with glucose concentration or level is referred to as a short-term implantable device. Conversely, devices such as a lancet, applied current, laser poration, or suction are referred to as either a traditional invasive or alternative invasive technique as they do not fulfill both the three hour and penetration of skin parameters. An example of a short-term implantable glucose analyzer is MiniMed's® continuous glucose monitoring system. In this document, long-term implantables are distinguished from short-term implantables by having the criteria that they must both penetrate the skin and be used for a period of one month or longer. Long term implantables may be in the body for greater than one month, one year, or many years.

Implantable glucose analyzers vary widely, but have at least several steps in common. First, at least part of the device penetrates the skin. More commonly, the entire device is imbedded into the body. Second, the apparatus is used to acquire either a sample of the body or a signal relating directly or based upon direct reactions occurring with the glucose concentration within the body. If the implantable device collects a sample, readings or measurements on the sample may be collected after removal from the body. Alternatively, readings may be transmitted out of the body by the device or used for such purposes as insulin delivery while in the body. Third, an algorithm is used to convert the signal into a reading directly or based upon direct reactions occurring with the glucose concentration. An implantable analyzer may read from one or more of a variety of body fluids or tissues including but not limited to: arterial blood, venous blood, capillary blood, interstitial fluid, and selectively sampled interstitial fluid. An implantable analyzer may also collect glucose information from skin tissue, cerebral spinal fluid, organ tissue, or through an artery or vein. For example, an implantable glucose analyzer may be placed transcutaneously, in the peritoneal cavity, in an artery, in muscle, or in an organ such as the liver or brain. The implantable glucose sensor may be one component of an artificial pancreas.

Description of Related Technology

One class of alternative invasive continuous glucose monitoring systems are those based upon iontophoresis. Using the iontophoresis process, uncharged molecules such as glucose may be moved across the skin barrier with the application of a small electric current. Several patents and publications in this area are available (Tamada, J. A., S. Garg, L. Jovanovic, K. R. Pitzer, S. Fermi, R. O. Potts, "Noninvasive Glucose Monitoring Comprehensive Clinical Results," *JAMA*, Vol. 282, No. 19, pp. 1839-1844, Nov. 17, 1999; Berner, Bret; Dunn, Timothy c.; Farinas, Kathleen C.; Garrison, Michael D.; Kurnik, Ronald T.; Lesho, Matthew J.; Potts, Russell O.; Tamada, Janet A.; Tierney, Michael J. "Signal Processing for Measurement of Physiological Analysis", U.S. Pat. No. 6,233,471, May 15, 2001; Dunn, Timothy C.; Jayalakshmi, Yalia; Kurnik, Ronald T.; Lesho, Matthew J.; Oliver, Jonathan James; Potts, Russell O.; Tamada, Janet A.; Waterhouse, Steven Richard; Wei, Charles W. "Microprocessors for use in a Device Predicting Physiological Values", U.S. Pat. No. 6,326,160, Dec. 4, 2001; Kurnik, Ronald T. "Method and Device for Predicting Physiological Values", U.S. Pat. No. 6,272,364, Aug. 7, 2001; Kurnik, Ronald T.; Oliver, Jonathan James; Potts, Russell O.; Waterhouse, Steven Richard; Dunn, Timothy C.; Jayalakshmi, Yalia; Lesho, Matthew J.; Tamada, Janet A.; Wei, Charles W. "Method and Device for Predicting Physiological Values", U.S. Pat. No. 6,180,416, Jan. 30, 2001; Tamada, Janet A.; Garg, Satish; Jovanovic, Lois; Pitzer, Kenneth R.; Fermi, Steve; Potts, Russell O. "Noninvasive Glucose Monitoring", JAMA, 282, 1999, 1839-1844; Sage, Burton H. "FDA Panel Approves Cygnus's Noninvasive GlucoWatch™", Diabetes Technology & Therapeutics, 2, 2000, 115-116; and "GlucoWatch Automatic Glucose Biographer and AutoSensors", Cygnus Inc., Document #1992-00, Rev. March 2001) The Cygnus Glucose Watch® uses this technology. The GlucoWatch® provides only one reading every twenty minutes, each delayed by at least ten minutes due to the measurement process. The measurement is made through an alternative invasive electrochemical-enzymatic sensor on a sample of interstitial fluid which is drawn through the skin using iontophoresis. Consequently, the limitations of the device include the potential for significant skin irritation, collection of a biohazard, and a limit of three readings per hour.

One class of semi-implantable glucose analyzers are those based upon open-flow microperfusion (Trajanowski, Zlatko; Brunner, Gernot A.; Schaupp, Lucas; Ellmerer, Martin; Wach, Paul; Pieber, Thomas R,; Kotanko, Peter; Skrabai, Falko "Open-Flow Microperfusion of Subcutaneous Adipose Tissue for ON-Line Continuous Ex Vivo Measurement of Glucose Concentration", Diabetes Care, 20, 1997, 1114-1120). Typically these systems are based upon biosensors and amperometric sensors (Trajanowski, Zlatko; Wach, Paul; Gfrerer, Robert "Portable Device for Continuous Fractionated Blood Sampling and Continuous ex vivo Blood Glucose Monitoring", Biosensors and Bioelectronics, 11, 1996, 479-487). A common issue with semi-implantable and implantable devices is coating by proteins. The MiniMed® continuous glucose monitoring system, a short-term implantable, is the first commercially available semi-continuous glucose monitor in this class. The MiniMed® system is capable of providing a glucose profile for up to seventy-two hours. The system records a glucose value every five minutes. The technology behind the MiniMed® system relies on a probe being invasively implanted into a subcutaneous region followed by a glucose oxidase based reaction producing hydrogen peroxide, which is oxidized at a platinum electrode to produce an analytical current. Notably, the MiniMed® system automatically shifts glucose determinations by ten minutes in order to accommodate for a potential dynamic lag between the blood and interstitial glucose (Gross, Todd M.; Bode, Bruce W.; Einhorn, Daniel; Kayne, David M.; Reed, John H.; White, Neil H.; Mastrototaro, John J. "Performance Evaluation of the MiniMed Continuous Glucose Monitoring System During Patient Home Use", Diabetes Technology & Therapeutics, 2, 2000, 49-56.; Rebrin, Kerstin; Steil, Gary M.; Antwerp, William P. Van; Mastrototaro, John J. "Subcutaneous Glucose Predicts Plasma Glucose Independent of Insulin: Implications for Continuous Monitoring", Am., J. Physiol., 277, 1999, E561-E571, 0193-1849/99, The American Physiological Society, 1999).

Other approaches, such as the continuous monitoring system reported by Gross, et. al. (Gross, T. M., B. W. Bode, D. Einhorn, D. M. Kayne, J. H. Reed, N. H. White and J. J. Mastrototaro, "Performance Evaluation of the MiniMed® Continuous Glucose Monitoring System During Patient Home Use," Diabetes Technology & Therapeutics, Vol. 2, Num. 1, 2000), involve the implantation of a sensor in tissue with a transcutaneous external connector. Inherent in these approaches are health risks due to the sensor implantation, infections, patient inconvenience, and measurement delay.

Another approach towards continuous glucose monitoring is through the use of fluorescence. For example Sensors for Medicine and Science Incorporated (S4MS) is developing a glucose selective indicator molecule combined into an implantable device that is coupled via telemetry to an external device. The device works via an indicator molecule that reversibly binds to glucose. With an LED for excitation, the indicator molecule fluoresces in the presence of glucose. This device is an example of a short-term implantable with development towards a long-term implantable (Colvin, Arthur E. "Optical-Based Sensing Devices Especially for In-Situ Sensing in Humans", U.S. Pat. No. 6,304,766, Oct. 16, 2001; Colvin, Arthur E.; Dale, Gregory A.; Zerwekh, Samuel, Lesho, Jeffery C.; Lynn, Robert W. "Optical-Based Sensing Devices", U.S. Pat. No. 6,330,464, Dec. 11, 2001; Colvin, Arthur E.; Daniloff, George Y.; Kalivretenos, Aristole G.; Parker, David; Ullman, Edwin E.; Nikolaitchik, Alexandre V. "Detection of Analytes by fluorescent Lanthanide Metal Chelate Complexes Containing Substituted Ligands", U.S. Pat. No. 6,334,360, Feb. 5, 2002; and Lesho, Jeffery "Implanted Sensor Processing System and Method for Processing Implanted Sensor Output", U.S. Pat. No. 6,400,974, Jun. 4, 2002).

Notably, none of these technologies are noninvasive. Further, none of these technologies offer continuous glucose determination.

Another technology, near-infrared spectroscopy, provides the opportunity to measure glucose noninvasively with a relativity short sampling interval. This approach involves the illumination of a spot on the body with near-infrared electromagnetic radiation (light in the wavelength range 700 to 2500 nm). The incident light is partially absorbed and scattered, according to its interaction with the constituents of the tissue. The actual tissue volume that is sampled is the portion of irradiated tissue from which light is diffusely reflected, transflected, or transmitted by the sample and optically coupled to the spectrometer detection system. The signal due to glucose is extracted from the spectral measurement through various methods of signal processing and one or more mathematical models. The models are developed through the process of calibration on the basis of an exemplary set of spectral measurements and associated reference blood glucose values (the calibration set) based on an analysis of capillary (fingertip), alternative invasive samples, or venous blood. To date, only discrete glucose determinations have been reported using near-IR technologies.

There exists a body of work on noninvasive glucose determination using near-IR technology, the most pertinent of which are referred here (Robinson, Mark Ries; Messerschmidt, Robert G "Method for Non-invasive Blood Analyte Measurement with Improved Optical Interface", U.S. Pat. No. 6,152,876, Nov. 28, 2000; Messerschmidt, Robert G.; Robinson, Mark Ries "Diffuse Reflectance Monitoring Apparatus", U.S. Pat. No. 5,935,062, Aug. 10, 1999; Messerschmidt, Robert G. "Method for Non-invasive Analyte Measurement with Improved Optical Interface", U.S. Pat. No. 5,823,951, Oct. 20, 1998; Messerschmidt, Robert G. "Method for Non-invasive Blood Analyte Measurement with Improved Optical Interface", U.S. Pat. No. 5,655,530; Rohrscheib, Mark; Gardner, Craig; Robinson, Mark R. "Method and Apparatus for Non-invasive Blood Analyte Measurement with Fluid Compartment Equilibration", U.S. Pat. No. 6,240, 306, May 29, 2001; Messerschmidt, Robert G.; Robinson, Mark Ries "Diffuse Reflectance Monitoring Apparatus", U.S. Pat. No. 6,230,034, May 8, 2001; Barnes, Russell H.; Brasch, Jimmie W. "Non-invasive Determination of Glucose Concentration in Body of Patients", U.S. Pat. No. 5,070,874, Dec. 10, 1991; and Hall, Jeffrey; Cadell, T. E. "Method and Device for Measuring Concentration Levels of Blood Constituents Non-invasively", U.S. Pat. No. 5,361,758, Nov. 8, 1994). Several Sensys Medical patents also address noninvasive glucose analyzers: Schlager, Kenneth J. "Non-invasive Near Infrared Measurement of Blood Analyte Concentrations", U.S. Pat. No. 4,882,492, Nov. 21, 1989.; Malin, Stephen; Khalil, Gamal "Method and Apparatus for Multi-Spectral Analysis in Noninvasive Infrared Spectroscopy", U.S. Pat. No. 6,040,578, Mar. 21, 2000; Garside, Jeffrey J.; Monfre, Stephen; Elliott, Barry C.; Ruchti, Timothy L.; Kees, Glenn Aaron "Fiber Optic Illumination and Detection Patterns, Shapes, and Locations for Use in Spectroscopic Analysis", U.S. Pat. No. 6,411,373, Jun. 25, 2002; Blank, Thomas B.; Acosta, George; Mattu, Mutua; Monfre, Stephen L. "Fiber Optic Probe and Placement Guide", U.S. Pat. No. 6,415,167, Jul. 2, 2002; and Wenzel, Brian J.; Monfre, Stephen L.; Ruchti, Timothy L.; Meissner, Ken; Grochocki, Frank "A Method for Quantification of Stratum Corneum Hydration Using Diffuse Reflectance Spectroscopy", U.S. Pat. No. 6,442,408, Aug. 27, 2002.

Mode of Analysis

A measurement of glucose is termed "direct" when the net analyte due to the absorption of light by glucose in the tissue is extracted from the spectral measurement through various methods of signal processing and/or one or more mathematical models. In this document, an analysis is referred to as direct if the analyte of interest is involved in a chemical reaction. For example, in equation 1 glucose reacts with oxygen in the presence of glucose oxidase to form hydrogen peroxide and gluconolactone. The reaction products may be involved in subsequent reactions such as that in equation 2. The measurement of any reaction component or product is a direct reading of glucose, herein. In this document, a direct reading of glucose would also entail any reading in which the electromagnetic signal generated is due to interaction with glucose or a compound of glucose. For example, the fluorescence approach listed above by Sensors for Medicine and Science is termed a direct reading of glucose, herein.

A measurement of glucose is termed "indirect" when movement of glucose within the body affects physiological parameters. In brief, an indirect glucose determination may be based upon a change in glucose concentration causing an ancillary physiological, physical, or chemical response that is relatively large. A key finding related to the noninvasive measurement of glucose is that a major physiological response accompanies changes in glucose and can be detected noninvasively through the resulting changes in tissue properties.

An indirect measurement of blood glucose through assessment of correlated tissue properties and/or physiological responses requires a different strategy when compared with the direct measurement of glucose spectral signals. Direct measurement of glucose requires the removal of spectral variation due to other constituents and properties in order to enhance the net analyte signal of glucose. Because the signal directly attributable to glucose in tissue is small, an indirect calibration to correlated constituents or properties, e.g. the physiological response to glucose, is attractive due to a gain in relative signal size. For example, changes in the concentration of glucose alters the distribution of water in the various tissue compartments. Because water has a large NIR signal that is relatively easy to measure compared to glucose, a calibration based at least in part on the compartmental activity of water has a magnified signal related to glucose. An indirect measurement may be referred to as a measurement of an ancillary effect of the target analyte. An indirect measurement means that an ancillary effect due to changes in glucose concentration is being measured.

A major component of the body is water. A re-distribution of water between the vascular and extravascular compartments and the intra- and extra-cellar compartments is observed as a response to differences in glucose concentrations in the compartments during periods of changing blood glucose. Water, among other analytes, is shifted between the tissue compartments to equilibrate the osmotic imbalance related to changes in glucose concentration as predicted by Fick's law of diffusion and the fact that water diffuses much faster in the body than does glucose. Therefore, a strategy for the indirect measurement of glucose that exploits the near-infrared signal related to fluid re-distribution is to design measurement protocols that force maximum correlation between blood glucose and the re-distribution of fluids. This is the opposite strategy of the one required for the direct measurement of blood glucose in which the near-infrared signals directly related to glucose and fluids must be discriminated and attempts at equalizing glucose in the body compartment are made. A reliable indirect measurement of glucose based at least in part in the re-distribution of fluids and analytes (other than glucose) and related changes in the optical properties of tissue requires that the indirect signals are largely due to the changing blood glucose concentration. Other variables and sources that modify or change the indirect signals of interest should be prevented or minimized in order to ensure a reliable indirect measurement of glucose.

One interference to a determination of blood/tissue glucose concentration measured indirectly is a rapid change in blood perfusion, which also leads to fluid movement between the compartments. This type of physiological change interferes constructively or destructively with the analyte signal of the indirect measurement. In order to preserve a blood glucose/fluid shift calibration it is beneficial to control other factors influencing fluid shifts including local blood perfusion.

Near-IR Instrumentation

A number of technologies have been reported for measuring glucose noninvasively that involve the measurement of a tissue related variable. One species of noninvasive glucose analyzers use some form of spectroscopy to acquire the signal or spectrum from the body. Examples include but are not limited to far-infrared absorbance spectroscopy, tissue impedance, Raman, and fluorescence, as well as techniques using light from the ultraviolet through the infrared [ultraviolet (200 to 400 nm), visible (400 to 700 nm), near-IR (700 to 2500 nm or 14,286 to 4000 $cm^{-1}$), and infrared (2500 to 14,285 nm or 4000 to 700 $cm^{-1}$)]. A particular range for noninvasive glucose determination in diffuse reflectance mode is about 1100 to 2500 nm or ranges therein (Hazen, Kevin H. "Glucose Determination in Biological Matrices Using Near-Infrared Spectroscopy", doctoral dissertation, University of Iowa, 1995). It is important to note, that these techniques are distinct from invasive techniques in that the sample analyzed is a portion of the human body in-situ, not a biological sample acquired from the human body. The actual tissue volume that is sampled is the portion of irradiated tissue from which light is diffusely reflected, transflected, or diffusely transmitted to the spectrometer detection system.

These techniques share the common characteristic that a calibration is required to derive a glucose concentration from subsequent collected data.

A number of spectrometer configurations exist for collecting noninvasive spectra of regions of the body. Typically a spectrometer has one or more beam paths from a source to a detector. A light source may include a blackbody source, a tungsten-halogen source, one or more LED's, or one or more laser diodes. For multi-wavelength spectrometers a wavelength selection device may be used or a series of optical filters may be used for wavelength selection. Wavelength selection devices include dispersive elements such as one or more plane, concave, ruled, or holographic grating. Additional wavelength selective devices include an interferometer, successive illumination of the elements of an LED array, prisms, and wavelength selective filters. However, variation of the source such as varying which LED or diode is firing may be used. Detectors may be in the form of one or more single element detectors or one or more arrays or bundles of detectors. Detectors may include InGaAs, extended InGaAs, PbS, PbSe, Si, MCT, or the like. Detectors may further include arrays of InGaAs, extended InGaAs, PbS, PbSe, Si, MCT, or the like. Light collection optics such as fiber optics, lenses, and mirrors are commonly used in various configurations within a spectrometer to direct light from the source to the detector by way of a sample. The mode of operation may be diffuse transmission, diffuse reflectance, or transflectance. Due to changes in performance of the overall spectrometer, reference wavelength standards are often scanned. Typically, a wavelength standard is collected immediately before or after the interrogation of the tissue or at the beginning of the day, but may occur at times far removed such as when the spectrometer was originally manufactured. A typical reference wavelength standard would be polystyrene or a rare earth oxide such as holmium, erbium, or dysprosium oxide. Many additional materials exist that have stable and sharp spectral features that may be used as a reference standard.

The interface of the glucose analyzer to the tissue includes a module where light such as near-infrared radiation is directed to and from the tissue either directly or through a light pipe, fiber-optics, a lens system, or a light directing mirror system. The area of the tissue surface to which near-infrared radiation is applied and the area of the tissue surface the returning near-infrared radiation is detected from are different and separated by a defined distance and selected to target a tissue volume conducive for the measurement of the property of interest. The patient interface module may include an elbow rest, a wrist rest, a hand support, and/or a guide to assist in interfacing the illumination mechanism of choice and the tissue of interest. Generally, an optical coupling fluid is placed on the sampling surface to increase incident photon penetration into the skin and to minimize specular reflectance from the surface of the skin. Important parameters in the interface include temperature and pressure.

The sample site is the specific tissue of the subject that is irradiated by the spectrometer system and the surface or point on the subject the measurement probe comes into contact with. The ideal qualities of the sample site include homogeneity, immutability, and accessibility to the target analyte. Several measurement sites may be used, including the abdomen, upper arm, thigh, hand (palm or back of the hand), ear lobe, finger, the volar aspect of the forearm, or the dorsal part of the forearm.

In addition, while the measurement can be made in either diffuse reflectance or diffuse transmittance mode, the preferred method is diffuse reflectance. The scanning of the tissue can be done continuously when pulsation effects do not affect the tissue area being tested, or the scanning can be done intermittently between pulses.

The collected signal (near-infrared radiation in this case) is converted to a voltage and sampled through an analog-to-digital converter for analysis on a microprocessor based system and the result displayed.

Preprocessing

Several approaches exist that employ diverse preprocessing methods to remove spectral variation related to the sample and instrumental variation including normalization, smoothing, derivatives, multiplicative signal correction (Geladi, P., D. McDougall and H. Martens. "Linearization and Scatter-Correction for Near-infrared Reflectance Spectra of Meat," *Applied Spectroscopy*, vol. 39, pp. 491-500, 1985), standard normal variate transformation (R. J. Barnes, M. S. Dhanoa, and S. Lister, *Applied Spectroscopy*, 43, pp. 772-777, 1989), piecewise multiplicative scatter correction (T. Isaksson and B. R. Kowalski, *Applied Spectroscopy*, 47, pp. 702-709, 1993), extended multiplicative signal correction (H. Martens and E. Stark, *J. Pharm Biomed Anal*, 9, pp. 625-635, 1991), pathlength correction with chemical modeling and optimized scaling ("GlucoWatch Automatic Glucose Biographer and AutoSensors", Cygnus Inc., Document #1992-00, Rev. March 2001), and FIR filtering (Sum, S. T., "Spectral Signal Correction for Multivariate Calibration," Doctoral Dissertation, University of Delaware, Summer 1998; Sum, S. and S. D. Brown, "Standardization of Fiber-Optic Probes for Near-Infrared Multivariate Calibrations," *Applied Spectroscopy*, Vol. 52, No. 6, pp. 869-877, 1998; and T. B. Blank, S. T. Sum, S. D. Brown and S. L. Monfre, "Transfer of near-infrared multivariate calibrations without standards," *Analytical Chemistry*, 68, pp. 2987-2995, 1996). In addition, a diversity of signal, data or pre-processing techniques are commonly reported with the fundamental goal of enhancing accessibility of the net analyte signal (Massart, D. L., B. G. M. Vandeginste, S. N. Deming, Y. Michotte and L. Kaufman, *Chemometrics: a textbook*, New York: Elsevier Science Publishing Company, Inc., 215-252, 1990; Oppenheim, Alan V. and R. W. Schafer, *Digital Signal Processing*, Englewood Cliffs, N.J.: Prentice Hall, 1975, pp. 195-271; Otto, M., *Chemometrics*, Weinheim: Wiley-VCH, 51-78, 1999; Beebe, K. R., R. J. Pell and M. B. Seasholtz, *Chemometrics A Practical Guide*, New York: John Wiley & Sons, Inc., 26-55, 1998; M. A. Sharaf, D. L. Illman and B. R. Kowalski, *Chemometrics*, New York: John Wiley & Sons, Inc., 86-112, 1996; and Savitzky, A. and M. J. E. Golay. "Smoothing and Differentiation of Data by Simplified Least Squares Procedures," Anal. Chem., vol. 36, no. 8, pp. 1627-1639, 1964). The goal of all of these techniques is to attenuate the noise and instrumental variation without affecting the signal of interest.

While methods for preprocessing effectively compensate for variation related to instrument and physical changes in the sample and enhance the net analyte signal in the presence of noise and interference, they are often inadequate for compensating for the sources of tissue related variation. For example, the highly nonlinear effects related sampling different tissue locations can't be effectively compensated for through a pathlength correction because the sample is multi-layered and heterogeneous. In addition, fundamental assumptions inherent in these methods, such as the constancy of multiplicative and additive effects across the spectral range and homoscadasticity of noise are violated in the non-invasive tissue application.

Near-IR Calibration

One noninvasive technology, near-infrared spectroscopy, has been heavily researched for its application for both frequent and painless noninvasive measurement of glucose. This approach involves the illumination of a spot on the body with near-infrared (NIR) electromagnetic radiation, light in the wavelength range of 700 to 2500 nm. The light is partially absorbed and scattered, according to its interaction with the constituents of the tissue. With near-infrared spectroscopy, a mathematical relationship between an in-vivo near-infrared measurement and the actual blood glucose value needs to be developed. This is achieved through the collection of in-vivo NIR measurements with corresponding blood glucose values that have been obtained directly through the use of measurement tools such as the YSI, HemoCue, or any appropriate and accurate traditional invasive or alternative invasive reference device.

For spectrophotometric based analyzers, there are several univariate and multivariate methods that can be used to develop this mathematical relationship. However, the basic equation which is being solved is known as the Beer-Lambert Law. This law states that the strength of an absorbance/reflectance measurement is proportional to the concentration of the analyte which is being measured as in equation 3, $$A = \epsilon b C \qquad \text{eq. 3}$$

where A is the absorbance/reflectance measurement at a given wavelength of light, $\epsilon$ is the molar absorptivity associated with the molecule of interest at the same given wavelength, b is the distance (or pathlength) that the light travels, and C is the concentration of the molecule of interest (glucose).

Chemometric calibration techniques extract the glucose related signal from the measured spectrum through various methods of signal processing and calibration including one or more mathematical models. The models are developed through the process of calibration on the basis of an exemplary set of spectral measurements known as the calibration set and an associated set of reference blood glucose values based upon an analysis of fingertip capillary blood, venous, or alternative site samples. Common multivariate approaches requiring a set of exemplary reference glucose concentrations and an associated sample spectrum include partial least squares (PLS) and principal component regression (PCR). Many additional forms of calibration are well known in the art such as neural networks.

Because every method has error, it is beneficial that the primary device, which is used to measure blood glucose be as accurate as possible to minimize the error that propagates through the mathematical relationship which is developed. While it appears intuitive that any U.S. FDA approved blood glucose monitor could be used, for accurate verification of the secondary method a monitor which has an accuracy of less than 5% is desirable. Meters with increased error such as 10% are acceptable, though the error of the device being calibrated may increase.

Currently, no device using near-infrared spectroscopy for the noninvasive measurement of glucose has been approved for use by persons with diabetes due to technology limitations that include poor sensitivity, sampling problems, time lag, calibration bias, long-term reproducibility, stability, and instrument noise. Fundamentally, however, accurate noninvasive estimation of blood glucose is presently limited by the available near-infrared technology, the trace concentration of glucose relative to other constituents, and the dynamic nature of the skin and living tissue of the patient. Further limitations to commercialization include a poor form factor (large size, heavy weight, and no or poor portability) and usability. For example, existing near-infrared technology is limited to larger devices that do not provide (nearly) continuous or automated measurement of glucose and are difficult for consumers to operate.

Clearly, a need exists for a completely noninvasive approach to the measurement of glucose that provides a nearly continuous readings in an automated fashion.

SUMMARY OF THE INVENTION

The invention involves the monitoring of a biological parameter through a compact analyzer. The preferred apparatus is a spectrometer based system that is attached continuously or semi-continuously to a human subject and collects spectral measurements that are used to determine a biological parameter in the sampled tissue. The preferred target analyte is glucose. The preferred analyzer is a near-IR based glucose analyzer for determining the glucose concentration in the body.

BRIEF DESCRIPTION OF THE DRAWINGS

FIG. 8 shows an LED based embodiment of the sampling module;

FIG. 9 shows a possible LED reflector; and

FIG. 10 shows filter shapes optionally coupled to the LED.

DETAILED DESCRIPTION OF A PREFERRED EMBODIMENT

Figure 1:
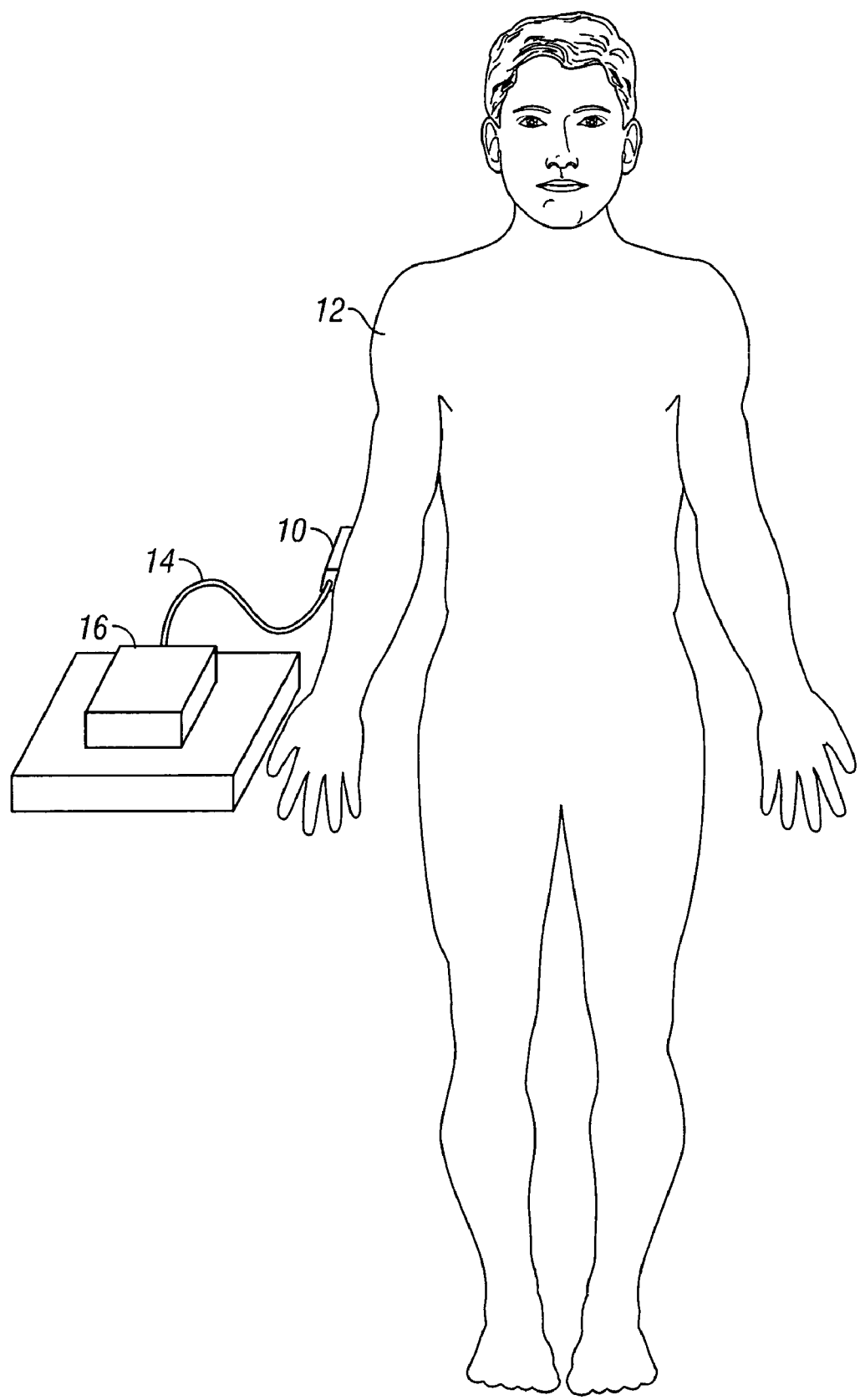
FIG. 1 shows a sampling module, a communication bundle and a base module.

The presently preferred embodiment of the invention uses a sampling module coupled to a base module. The sampling module includes an illumination system based upon an incandescent lamp. The base module includes a grating and detector array. The base module may be connected to the sampling module through a communication bundle. In this document, the combined sampling module, communication bundle, base module, and associated electronics and software is referred to as a spectrometer and/or glucose analyzer. In FIG. 1, the sampling module 10 is semi-permanently attached to the forearm of a subject 12, a communication bundle 14 carries optical and/or electrical signal to and/or from a base module 16 located on a table, and the communication bundle carries power to the sampling module from the base module.

Figure 2:
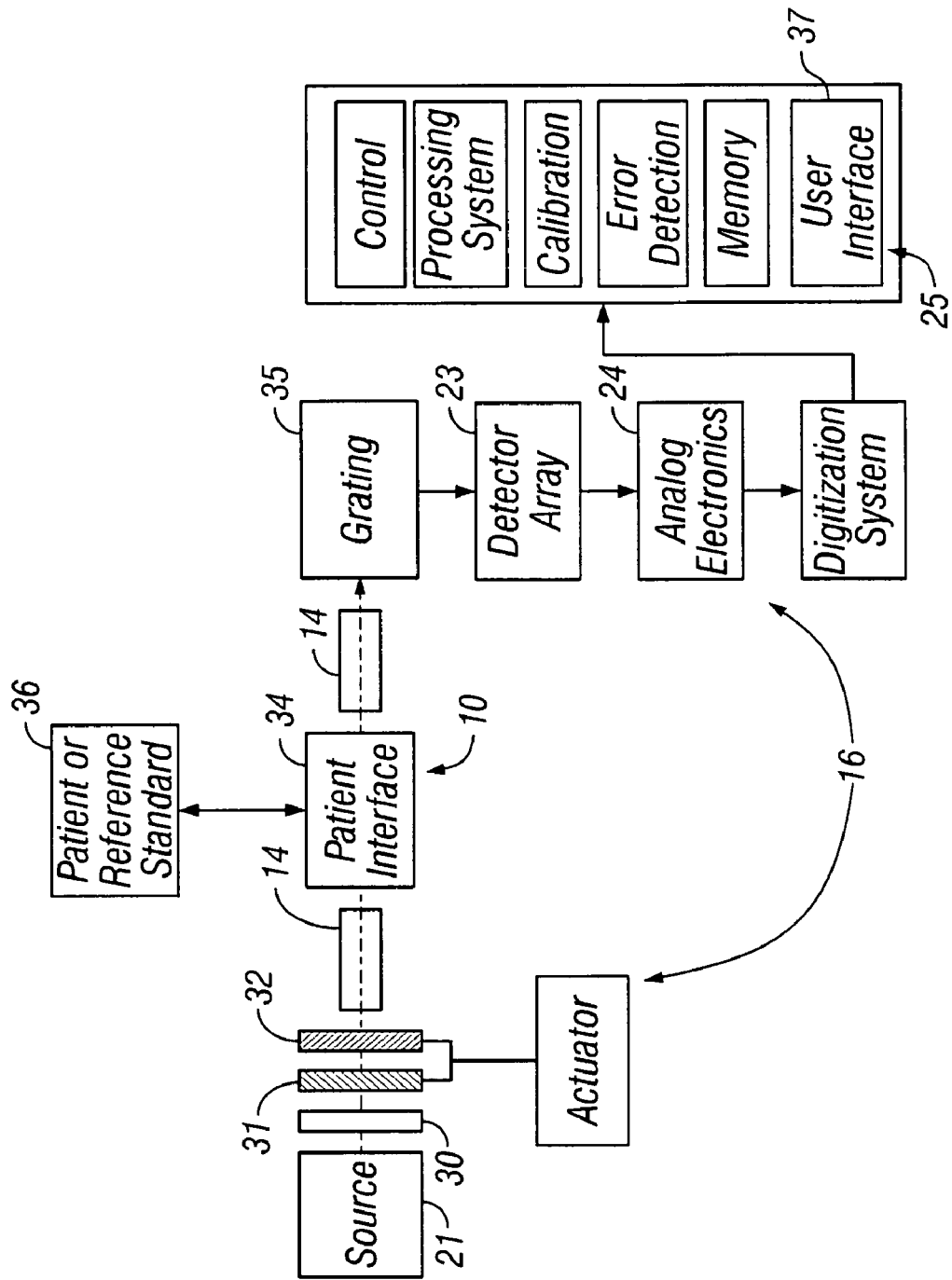
FIG. 2 shows a preferred embodiment with a grating and detector array.

A block diagram of the noninvasive glucose analyzer is provided in FIG. 2. Essential elements of the glucose analyzer are the source 21, guiding optics 14 before and/or after the sample for coupling the source to the sample and the sample to the detector(s) 23, detector(s) and associated electronics 24, and data processing system 25. In FIG. 2, an optional optical filter 30, light blocker 31, and standardization material 32 are shown. These components may also be positioned after the sample and before the detector. Variations of this simple block diagram are readily appreciated and understood by those skilled in the art.

The sampling module, base module, and communication bundle are further described herein. Key features of the invention may include but are not limited to: a semi-permanent patient/instrument interface sampling module 10 incorporating at least one of a low profile sampling interface 34, a low wattage stabilized source 21 in close proximity to the sampled site, an excitation collection cavity or optics, a guide, a preheated interfacing solution such as fluorinert, a temperature controlled skin sample, a mechanism for constant pressure and/or displacement of the sampled skin tissue, a photonic stimulation source, and collection optics or fiber.

In the preferred embodiment the sampling module protrudes less than two centimeters from the skin measurement site. The sampling module may interface with a guide that may be semi-permanently attached to a sampling location on a human body. The guide aids in continuously and/or periodically physically and optically coupling the sampling module to the tissue measurement site in a repeatable manner with minimal disturbance. In addition, the guide in combination with the sampling module is responsible for pretreatment of the sample site for providing appropriate contact of the sampling device to the skin for the purpose of reducing specular reflectance, approaching and maintaining appropriate skin temperature variation, and inducing skin hydration changes. The sampling module preferably collects a diffusely reflected or transflected signal from the sampled region of skin.

In the preferred embodiment, the base module or semi-remote system includes at least a wavelength selection device such as a grating 35 and a detector preferably a detector array with an optional wavelength reference standard 36 such as polystyrene and an optional intensity reference standard such as a 99% reflective Labsphere® disk. The remote system is coupled to the sampling module via a communication bundle 14 that carries as least the optical signal and optionally power. Additionally, the communication bundle may transmit control and monitoring signal between the sampling module and the remote system. The remote system has at least one of an embedded computer 25, a display 37, and an interface to an external computer system. The remote system may be in close proximity to the guide element.

In one version of the invention, the sampling module and base module are integrated together into a compact handheld unit. The communication bundle is integrated between the two systems.

Figure 3:
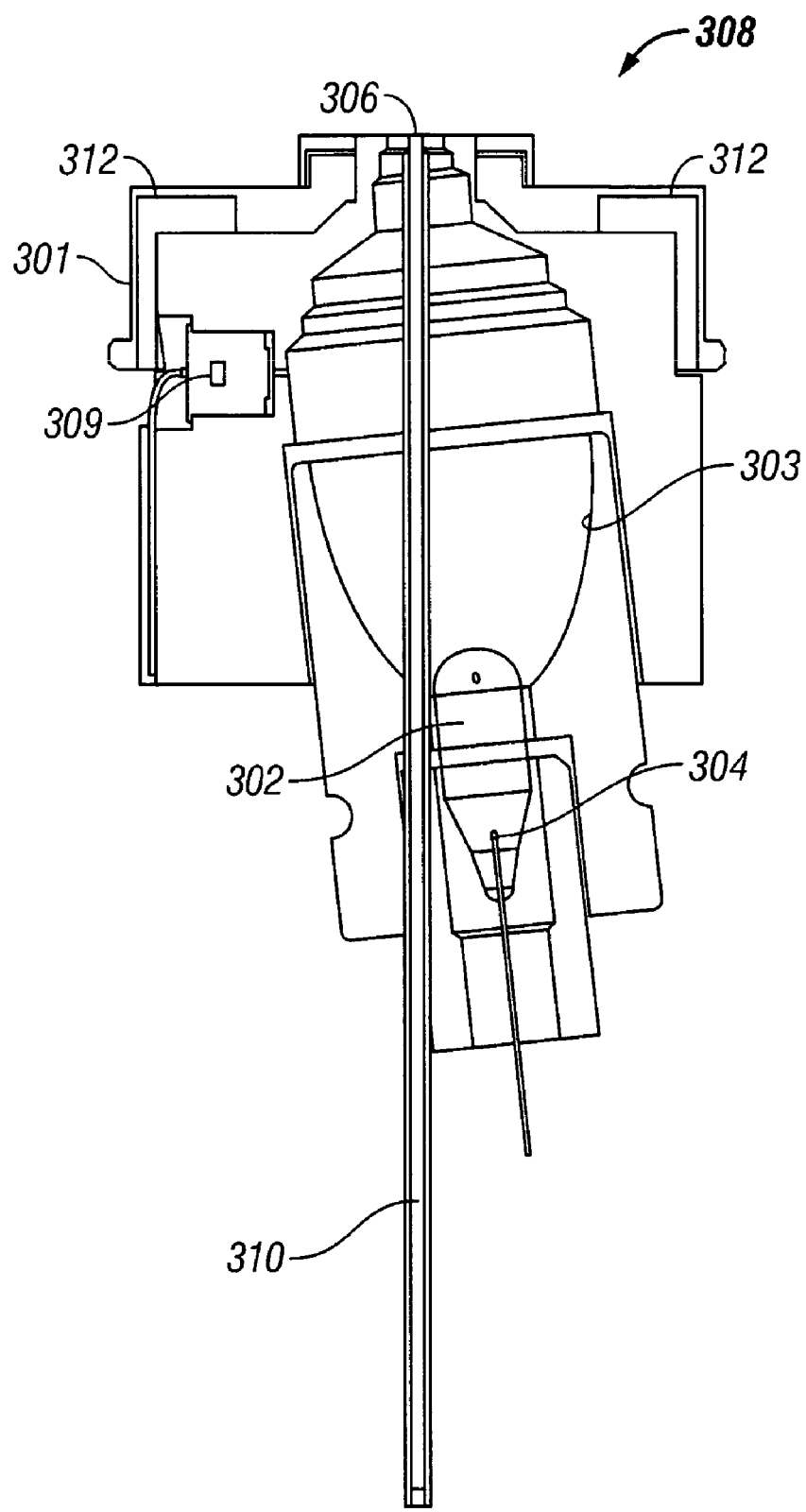
FIG. 3 shows a preferred embodiment of the sampling module.

One version of the sampling module of the invention is presented in FIG. 3. The housing 301 is made of silicon. The lamp 302 is a 0.8 W tungsten halogen source (Welch-Allyn 01270) coupled to a reflector 303. A photodiode 309 is used to monitor the lamp and to keep its output stable through the use of a lamp output control circuit, especially right after power-up. The reflector, and hence the incident light, is centered on an angle six degrees off of the skin's normal to allow room for a collection fiber. The light is focused through a 1 mm thick silicon window 306 onto an aperture at the skin. The silicon operates as a longpass filter. The illuminated aperture of the skin has a 2.4 mm diameter. Positioning onto a sampling site is performed through a guide. The patient sampling module reversibly couples into the guide for reproducible contact pressure and sampling location. Magnets 312 are used in the guide to aid in the positioning of the probe, to ensure proper penetration of the probe into the guide aperture and to enable a constant pressure and/or displacement interface of the sampled skin 308. The reversible nature of coupling the sampling module into the guide allows the sampling module to be removed and coupled to an intensity reference and/or a wavelength reference that have the same guide interface and are preferably housed with the base module. The preferred intensity reference is a 99% reflective Labsphere® material and the preferred wavelength reference is polystyrene. The preferred sampling module uses a heater 309 for maintaining the skin at a constant temperature. A 600 μm detection fiber 310 collects diffusely reflected light from the center of the silicon window. The detection fiber is coated in a manner to block source photons from penetrating through the cladding to the core. For example a metal sheath may be placed around the detection fiber. In this configuration, the length of the detection fiber is 0.7 meters. The communication bundle includes a power supply from the base unit. A blocking mechanism may be included to allow the detection of detector dark current or baseline. The base module incorporating a grating, detected array, associated electronics, and associated software is coupled to the sampling module via this bundle. In this configuration, the sampling module extends roughly three inches from the arm.

It should be appreciated that in the preferred embodiment, many of the components are optional and/or variable. Some specific variations are described in this section. It is recognized that the components or properties discussed in this section may be varied or in some cases eliminated without altering the scope and intent of the invention.

In the preferred embodiment, the base module resides on a table, the sampling module interfaces through a semi-permanently attached guide to the dorsal aspect of the forearm, and a communication bundle carries power and optical signal between the two modules. Alternatively, the base module may be worn on the person, for example on a belt. The sampling module could couple to any of a hand, finger, palmar region, base of thumb, forearm, volar aspect of the forearm, dorsal aspect of the forearm, upper arm, head, earlobe, eye, tongue, chest, torso, abdominal region, thigh, calf, foot, plantar region, and toe. When the base module is on the table, it may plug into a standard wall outlet for power. When worn on the person, the module may be battery powered. When the base module is worn on the person, an optional docking station may be provided as described below for power and data analysis. It is noted here that the base module may couple directly to the sampling module without a communication bundle. The combined base module and sampling module may be integrated into a handheld near-IR based glucose analyzer that couples to the sampling site through an optional guide.

Sampling Module

The sampling module housing in the preferred embodiment was selected to be constructed of silicon based upon a number of factors including but not limited to: providing a minimum of 6 O.D. blocking in the ultraviolet, visible, and near-IR from 700 to 1000 nm at a 1 mm thickness, low cost, manufacturability, durability, water resistance, and availability. It is recognized that it is the functionality of the housing that is important and that the above listed properties may be obtained through a variety of materials such as metals, composites, and plastics without altering the scope and intent of the invention.

The 0.8 W tungsten halogen source is preferred for a number of reasons including but not limited to its power requirements, performance specifications such as color temperature, spectral output, and lifetime as well as on parameters such as ruggedness, portability, cost, and size. It is recognized that the source power is selected based upon the total net analyte signal generated and the amount of light reaching the detection system. It has been determined that the 0.8 W source in conjunction with the aperture and collection fiber of the preferred embodiment provides adequate signal and depth of penetration of the photons for the indirect determination of glucose using features in the 1150 to 1850 nm range. However, sources ranging from 0.05 W to 5 W may be used in this invention. As described in the alternative embodiment section, light emitting diodes (LED's) may be used as the source. The source is preferably powered by the base module through the connection cable described below. However, especially with the smaller sources a battery power supply may be incorporated into the sampling module.

A photodiode is used in the preferred embodiment in conjunction with feedback control electronics to maintain the source at constant power output during data collection which is desirable during data acquisition. The photodiode is placed before the order sorter (the silicon longpass filter), in order to detect visible light from the source. The preferred photodiode is a silicon detector. Other less desirable photodiodes include but are not limited to InGaAs, InPGaAs, PbS, and PbSe. This arrangement of components is preferred due to the low cost, durability, and availability of detectors available in the visible and near-IR from 700 to 1000 nm where the long pass filter discussed below used later in the optical train blocks the optical signal used in the feedback loop. The control electronics allow the source to be driven at different levels at different points in time during and prior to data acquisition. In the preferred embodiment, the source is initially run at a higher power in order to minimize the analyzer warm-up time. The photodiode and feedback electronics are optional, but are used in the preferred embodiment. Many spectrometers are common in the art that do not use a separate detector for monitoring the source intensity.

The source housing/reflector combination in the preferred embodiment was selected based upon a number of factors including but not limited to: providing acceptable energy delivery to the sample site, reflectivity, manufacturability, ruggedness, size, cost, and providing appropriate heating/temperature control of the sample site. The specific reflector in the preferred embodiment is parabolic. The properties were optimized using standard ray trace software to image the lamp filament onto the aperture defining the sampling location. The optical prescription is tuned for a specific spectral range (1100 to 1900 nm) and the coatings are designed to reflect optimally in this range. It is recognized that the reflector may be elliptical or even spherical and that the mechanical and optical properties of the reflector may be varied without altering the scope and intent of the invention. For example, in the simplest embodiment the source may shine light directly onto the sampled surface without the use of a reflector. In such cases, in order to deliver similar energy to the sampled skin through the aperture, a larger source is required. In another example, the specific focal distance of the reflector may be varied, which impacts the overall dimensions of the interface without affecting functionality. Similarly, a different substrate may be used as the reflector or metallized coatings such as gold, silver, and aluminum may be applied to the substrate.

Figure 4:
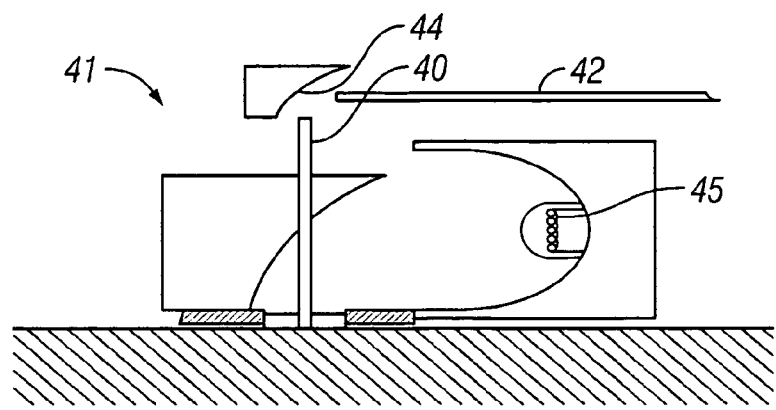
FIG. 4 shows a low profile embodiment of the sampling module.

The source/housing reflector in the preferred embodiment may be modified to bring in the source light nearly parallel to the skin surface. One objective of a low profile design is to maintain a sampling module that may be semi-permanently attached to the sampling site. A low profile sampling module has the benefit of increase acceptance by the consumer and is less susceptible to bumping or jarring during normal wear. A semi-permanent interface would allow consecutive glucose determinations in an automated continuous or semi-continuous fashion as described below. Light brought in at a low angle relative to the skin may be turned into the skin with folding optics. A simple mirror may be used; however, a focusing mirror is preferred in order to optimally couple light into the aperture. A representative embodiment is provided in FIG. 4.

One feature that may be used in this embodiment and in the other embodiments is the use of quick connect optics. In this case a 600 µm fiber 40 is used as the collection optic. The 600 µm fiber is fixed into the sampling module 41. The sampling module has a connector for accepting a 300 µm fiber 42 that in turn couples to a slit prior to the grating in the base module. The coupling of the light may be done by lenses, which may be magnifying or de-magnifying or with folding mirrors 44 with appropriate attention to matching numerical apertures. An important concept in this design is that the second collection optic is readily removed from the sampling module allowing the sampling module to remain in contact with the arm. In addition, the quick connect optic allows the user to travel remotely from the base module until the next reading is desired.

Locating the source and reflector housing near the skin allows for temperature control/warm-up of the skin. The optical source is a heat source. Skin temperature is an important variable in near-IR noninvasive glucose determination. A thermistor 45 sensing the sampling module or patient skin temperature and feeding this information back to the source via feedback electronics prior to sampling may be used prior spectral data acquisition in order elevate the skin temperature to a desirable sampling range such as 30 to 40 degrees centigrade. The inclusion of a heater, thermistor, and associated feedback electronics are optional to this invention. In another embodiment, the skin temperature may be measured spectrally by the relative positions of water, fat, and protein in an acquired near-IR spectrum or through a multivariate analysis.

In the preferred embodiment, an optical filter is placed between the source and the sampling site. In the preferred embodiment, the optical filter is silicon. The silicon window was selected based upon a number of factors. One factor is that silicon behaves as a longpass filter with blocking to at least six optical density units with a 1 mm thickness from the ultraviolet through the visible to 1000 nm. Second, the longpass characteristic of silicon acts as an order sorter benefiting the grating detector combination in the base module. Third, longpass characteristics of silicon removes unwanted photons in the ultraviolet, visible, and near-IR that would heat the skin at unwanted depths and to undesirable temperatures due to conversion of the light into heat via the process of absorbance. Instead, the silicon is heated by these photons resulting in maintenance of skin temperature near the surface via conduction. Fourth, silicon offers excellent transmissive features in the near-IR over the spectral region of interest of 1150 to 1850 nm. Notably, silicon is the same material as the source housing and source reflector. Therefore, a single molding or part may be used for all three components. In the preferred embodiment, a silicon window is in contact with the skin to minimize specular reflectance. In the preferred embodiment, this window is anti-reflection coated based upon properties of air on the photon incident side and based upon the optical properties of the coupling fluid on the skin surface side of the optic.

Many configurations exist in which the longpass filter is not in direct contact with the skin. First, the longpass filter may be placed after the source but not in contact with the skin. For example, the filter may be placed in or about the pupil plane. In this configuration, photons removed by the filter that result in the heating of the filter do not result in direct heating of the sample site via conduction. Rather, the much slower and less efficient convection process conveys this heat. This reduces the risk of over heating the skin. Alternatively, two filters may be placed between the source and the skin. These filters may or may not be the same. The first filter removes heat as above. The second filter reduces spectral reflectance as above. In a third configuration, the order sorter nature of the longpass filter is central. Silicon removes light under 1050 nm. This allows a grating to be used in the 1150 to 1850 nm region without the detection of second or higher order light off of the grating as long as the longpass filter, silicon, is placed before the grating. Therefore, in the third configuration the longpass filter may be after the sample.

Figure 5:
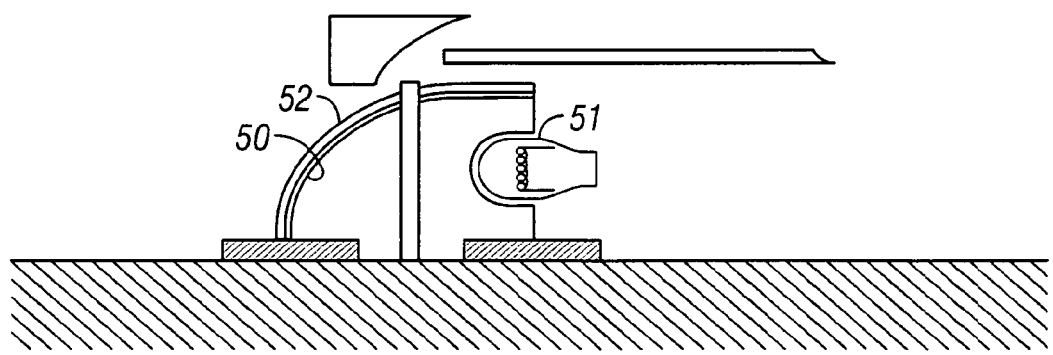
FIG. 5 shows a single filter embodiment of the sampling module.

It is recognized that many filter designs exist. In the preferred embodiment a silicon longpass filter is used. The filters may be coated to block particular regions such as 1900 to 2500 nm, antireflection-coated in order to match refractive indices and increase light throughput, and/or used in combination with other filters such as shortpass filters. One configuration coats the silicon with a blocker from 1900 to 2500 nm. This has the advantage of removing the largest intensity of the blackbody curve of a typical tungsten halogen source that is not blocked by silicon or in the desirable region of 1150 to 1850 nm. This blocking band may cover any region from about 1800 nm on up to 3000 nm. Another configuration is a silicon longpass filter used in combination with an RG glass such as RG-850 that cuts off at about 2500 nm. The combination provides a very cost effective and readily reproduced bandpass filter passing light from approximately 1100 to 2500 nm. Notably this filter combination may be used in conjunction with a coating layer such as a blocker from 1900 to 2500 nm in order to provide a bandpass from 1100 to 1900 nm. Those skilled in the art will recognize that there exist multiple configurations of off the shelf and customized longpass, shortpass, and bandpass filter that may be placed in one or more of the locations described above that fulfill the utility requirements described above. An alternative embodiment of the source/reflector/filter is shown in FIG. 5. In this embodiment, silicon is shaped into a parabolic optic 50 surrounding part of the source 51. The outside of the silicon is coated with a reflector 52 such as gold. This embodiment allows a low profile source coupled to the skin. The total height off of the skin may be less than 1 cm with this configuration. The shape of the silicon optic in conjunction with coating the outside of the silicon with a reflective material such as gold allows efficient coupling of the photons into the skin. An additional optional protective coating over the reflector material allows the silicon optic to also act as a housing for the sampling module with the benefits of silicon listed above. Notably, the initial surface of the silicon (near the source) removes the higher energy photons that results in heating of the source optics prior to contact with the skin. The later part of the silicon (near the skin) in combination with a collection fiber acts as a mechanism for reducing specular reflectance. This configuration eliminates the optional two filter system as heat and spectral reflectance are dealt with in one optic. Essentially, the silicon is acting as a turning optic to allow a very low profile sampling module, as a longpass filter, as an order sorter, as a heat blocker, as a spectral reflectance blocker, and as a very manufacturable, cheap, and durable component.

Figure 6:
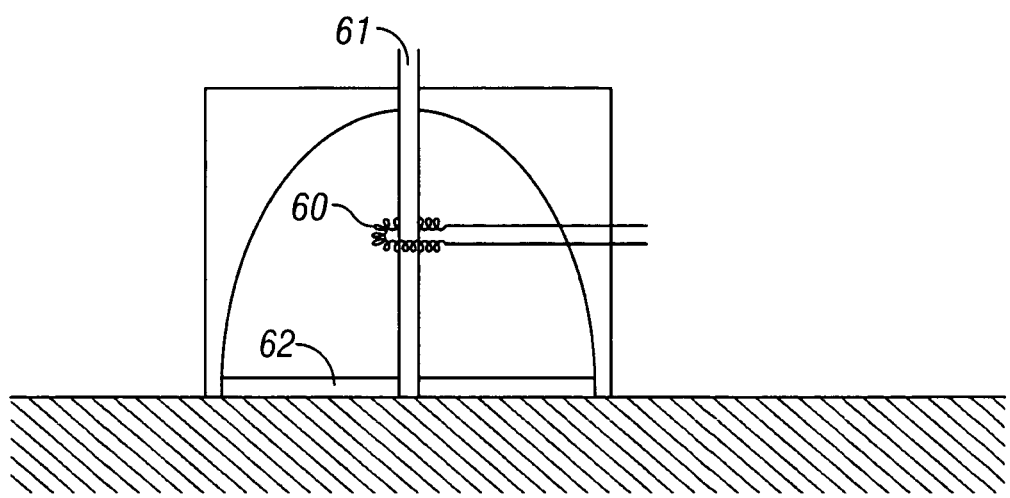
FIG. 6 shows an alternative embodiment of the sampling module.

An alternative embodiment of the source/reflector/filter is shown in FIG. 6. In this embodiment, the source filament 60 is wrapped around a collection fiber 61. The reflector now directs light into the skin aperture through an optic 62. The optic may be surface coated for reflectance on the incident light surface. Alternatively, as above, the reflector may be transmissive and the outer surface of the reflector may be reflectively coated. As above, this allow the reflector to act as the housing. In this embodiment, there exists a filter adjacent to the skin that in conjunction with a collection optic, fiber, or tube adjacent to the skin results in the blocking of specular reflectance.

An alternative embodiment combines a broadband source with a single element detector without the use of a grating. In one case, an interferometer composed of two parallel, highly reflecting plates separated by an air gap may be used. One of the parallel plates may be translated mechanically such that the distance between the plates varies. Technically, this is a Fabry-Perot interferometer. When the mirror distance is fixed and adjusted for parallelism by a spacer such as invar or quartz, the system is referred to as a Fabry-Perot etalon. This system allows narrow excitation lines as a function of time. Therefore, no dispersive element is required and a single element detector may be used. The interferometer may be placed in one of multiple positions in the optical train.

In the preferred embodiment, the illuminated aperture of the skin has a 2.4 mm diameter. The aperture in the preferred embodiment was selected based upon a number of factors including but not limited to: providing optical pathlengths within the sample for indirectly monitoring glucose concentrations within the body, providing acceptable energy delivery to the sample site, and providing appropriate heating/temperature control of the sample site. As discussed below, a fiber optic collection fiber is placed in the center of this illumination area. This allows the incident photon approximately 1 mm of radial travel from the point of illumination to the collection fiber. This translates into depths of penetration that probe water, fat, and protein bands as well as scattering effects that may be used for the indirect determination of glucose. It is recognized that the dimensions of the aperture need not be the exact dimensions of the preferred embodiment. An important aspect is the ability to deliver photons to a skin tissue, allow them to penetrate to depths that allow an indirect measurement of glucose, and detect those photons.

It is recognized that these properties may be varied without altering the scope and intent of the invention. For example, the aperture of 2.4 mm may be varied. The aperture provides an outer limit of where photons from the source may penetrate the skin. This in turn defines the largest depth of penetration and optical pathlengths observed. While the aperture may be varied from 1.2 to 5 mm in diameter, the 2.4 mm diameter allows collection of spectra with excellent features for the indirect measurement of glucose. At smaller apertures, the average depth of penetration of the collected photons decreases. Therefore, variation of the aperture affects the net analyte signal of the sampled tissue. Varying aperture shapes are possible as the shape affects the distribution of photons penetration depth and optical pathlength. The indirect determination of glucose may be performed off of sample constituents such as fat, protein, and water that are distributed as a function of depth. Therefore, the magnitude of the indirect signal varies with the aperture. In addition, multiple excitation sites and collection sites are possible. This could aid, for example, in sampling a representative section of the skin. For example, if one probe was located on a hair follicle, the others may be used independently or in conjunction with the first site in order to acquire the analytical signal necessary to determine glucose.

Guide

In the preferred embodiment, the entire PIM couples into a guide that is semi-permanently attached to the skin with a replaceable adhesive. The guide aids in sampling repeatability. The guide is intended to surround interfacing optics for the purpose of sampling in a precise location. Typically this is done with an interface surrounding the interface probe. In the main embodiment, the guide is attached for the waking hours of the subject. A guide may be attached in a more permanent fashion such as for a week or a month, especially in continuous monitoring glucose analyzers discussed below. The guide allows improved precision in sampling location. Precision in sampling location allows bias to be removed if a process such as mean centering is used in the algorithm. This is addressed in the preprocessing section below. Additionally, the guide allows for a more constant pressure/constant displacement to be applied to the sampling location which also enhances precision and accuracy of the glucose determination. While the guide greatly enhances positioning and allows associated data processing to be simpler and more robust, the guide is not an absolute requirement of the sampling module.

In the preferred embodiment of the invention, magnets are used to aid in a user friendly mechanism for coupling the sampling module to the sampled site. Further, the magnets allow the guide to be reversibly attached to the sampling module. Further, the guide aids in the optical probe adequately penetrating into the guide aperture. In addition, the magnets allow a constant, known, and precise alignment between the sampling probe and the sampled site. In the preferred embodiment two magnets are used, one on each side of the sampled site, in order to enhance alignment. One or more magnets may provide the same effect. It is recognized that there exist a large number of mechanical methods for coupling two devices together, such as lock and key mechanisms, electromagnets, machined fits, VELCRO, adhesives, snaps, and many other techniques commonly known to those skilled in the art that allow the key elements described above to be provided. In addition, the magnets may be electrically activated to facilitate a controlled movement of the probe into the guide aperture and to allow, through reversal of the magnet poles, the probe to be withdrawn from the guide without pulling on the guide.

The guide may optionally contain a window in the aperture that may be the longpass/bandpass filter. Alternatively, the aperture may be filled with a removable plug. The contact of a window or plug with the skin stabilizes the tissue by providing the same tissue displacement as the probe and increases the localized skin surface and shallow depth hydration. As opposed to the use of a removable plug, use of a contact window allows a continuous barrier for proper hydration of the sampling site and a constant pressure interface. The use of a plug or contact window leads to increased precision and accuracy in glucose determination by the removal of issues associated with dry or pocketed skin at the sampling site.

The guide may optionally contain any of a number of elements designed to enhance equilibration between the glucose concentration at the sampling site and a capillary site, such as the fingertip. Rapidly moving glucose values with time can lead to significant discrepancies between alternate site blood glucose concentration and blood glucose concentration in the finger. The concentration differences are directly related to diffusion and perfusion that combine to limit the rate of the equilibrium process. Equilibrium between the two sites allows for the use of glucose-related signal measured at an alternate site to be more accurate in predicting finger blood glucose values.

A number of optional elements may be incorporated into the sampling module and/or guide to increase sampling precision and to increase the net analyte signal for the indirect glucose determination. These optional elements are preferably powered through the base module and connection cable described below but may be battery operated. Equalization approaches include photonic stimulation, ultrasound pretreatment, mechanical stimulation, and heating. Notably, equilibration of the glucose concentration between the sampled site and a well-perfused region such as an artery or the capillary bed of the fingertip is not required. A minimization of the difference in glucose concentration between the two regions aids in subsequent glucose determination.

The guide may optionally contain an LED providing photonic stimulation about 890 nm, which is known to induce capillary blood vessel dilation. This technique may be used to aid in equilibration of alternative site glucose concentrations with those of capillary blood. By increasing the vessel dilation, and thereby the blood flow rate to the alternate site, the limiting nature of mass transfer rates and their effect on blood glucose differences in tissue is minimized. The resulting effect is to reduce the differences between the finger and the alternate site blood glucose concentrations. The preferred embodiment uses (nominally) 890 nm LED's in an array with control electronics set into the arm guide. The LED's can also be used in a continuous monitoring application where they are located in the probe sensing tip at the tissue interface. Due to the periods of excitation required for stimulation, the 890 nm LED is preferably powered by a rechargeable battery in the guide so that the LED may be powered when the communication bundle is not used.

The guide may optionally contain an apparatus capable of delivering ultrasound energy into the sample site. Again, this technique may be used to aid in equilibration of alternative site glucose concentrations with those of capillary blood by stimulating perfusion and/or blood flow.

The guide may optionally contain an apparatus that provides mechanical stimulation of the sampled site prior to spectral data acquisition. One example is a piezoelectric modulator than pulses in an out relative to the skin surface a distance of circa 20 to 50 µm in a continuous or duty cycle fashion.

The guide may optionally contain a heating and/or cooling element, such as a strip heater or an energy transfer pad. Heating is one mechanism of glucose compartment equilibration. These elements may be used to match the core body temperature, to manipulate the local perfusion of blood, to avoid sweating and/or to modify the distribution of fluids among the various tissue compartments.

It is recognized that the sampling module can interface directly to a skin sampling without the use of a guide.

In the preferred embodiment of the invention, a coupling fluid is used to efficiently couple the incident photons into the tissue sample. The preferred coupling fluid is fluorinert. Different formulations are available including FC-40 and FC-70. FC-40 is preferred. While many coupling fluids are available for matching refractive indices, fluorinert is preferred due to its non-toxic nature when applied to skin and due to its absence of near-IR absorbance bands that would act as interferences. In the preferred embodiment, the coupling fluid is preheated to between 90 and 95° F., preferably to 92° F. Preheating the coupling fluid minimizes changes to the surface temperature of the contacted site, thus minimizing spectral changes observed from the sampled tissue. The coupling fluid may be preheated using the source energy, the optional sample site heater energy, or through an auxiliary heat source. Preheating FC-70 is preferable due to its poorer viscosity. The preheated FC-70 is not as likely to run off of the sample site. Automated delivery prior to sampling is an option. Such a system could be a gated reservoir of fluorinert in the sample module. Manual delivery of the coupling fluid is also an option, such as a spray bottle delivery system. Coverage of the sample site is a key criteria in any delivery system.

In the preferred embodiment of the invention, the sampling site is the dorsal aspect of the forearm. In addition, the volar and ventral aspect of the forearm are excellent sampling locations. It is further recognized that the guide may be attached to other sampling locations such as the hand, fingertips, palmar region, base of thumb, forearm, upper arm, head, earlobe, chest, torso, abdominal region, thigh, calf, foot, plantar region, and toes. It is preferable but not required to sample regions of the skin that do not vary due to usage as with the fingertips or near joints, change with time due to gravity like the back of the upper arm, or have very thick skin such as the plantar region, or abdominal region.

There are a number of possible configurations for collection optics. In the preferred embodiment, light is incident to the sample through the longpass filter which is in contact with the skin. In the preferred embodiment, there exists a hole in the middle of the longpass filter. A collection fiber is placed into the hole in contact with the skin. This configuration forces incident photons into the sampled skin prior to collection into the fiber optic. If the fiber optic were merely pushed up against the filter, then light could bounce through the filter directly into the collection fiber without entering the skin resulting in a spectral reflectance term. Once the collection fiber is in contact with the skin, the signal (or rather absence of observed intensity) at the large water absorbance bands near 1450, 1900, and 2500 nm may be used to determine when the apparatus is in good spectral contact with the sampled skin. The preferred collection optic is a single 600 µm detection fiber. It is recognized that the hole and the fiber may be altered in dimension to couple in another sized fiber such as a 300 µm detection fiber. As those skilled in the art will appreciate, the fiber diameter is most efficient when it is optimally optically coupled to the detection system. Therefore, as detector systems slits and detector element sizes are varied, the collection optics should also be varied. The center collection fiber of 600 µm combined with the aperture of 2.4 mm is related to a central fiber collecting incident light from a bundle. The collection optic is not necessarily limited to a fiber optic. Additional configurations include but are not limited to a light pipe or a solid piece of optical glass.

In the preferred embodiment, the collected signal is turned 90° off axis to send the signal roughly parallel to the arm in order to minimize the height of the sampling module. This may be accomplished by such common means as a folding mirror or bending of a fiber optic, as described above.

In one embodiment, the collected light is coupled to a second collection that connects at its opposite end to the base module. The purpose of this configuration is to allow the sampling module to be worn on the person without the bulk of the rest of the spectrometer here referred to as the base module. A quick connect connector is used to allow rapid connection of the base module to the sampling module in a reproducible and user friendly fashion. The connecting cable carries at least the optical signal. In the preferred embodiment, the connection cable also carries power to the source and optional elements, such as the thermistor, heater, or sample compartment glucose concentration equilibration apparatus. This connector also allows the diameter of the collection fiber to be changed. For example, the 600 µm collection fiber may be downsized to a 300 µm connection fiber with appropriate attention to coupling optics and numerical apertures obvious to those skilled in the art. Some advantages of the smaller diameter connection fiber are described here. First, the smaller diameter fiber has a tighter bend radius. Second, if a slit is used prior to the spectrometer then the fiber can be made of appropriate dimension for coupling to the slit. Third, the smaller diameter fiber is less susceptible to breakage. An additional consideration is cost.

It is recognized that collection/detection elements may be recessed away from the window in order to avoid the direct detection of surface reflectance. It is further recognized that coupling fluids may be used to increase the angle of collection to the detection element.

Base Module

In the preferred embodiment, the base module includes at least a spectrometer (grating and detector system). The grating is optimized to deliver peak energy about 1600 nm. The detector is an InGaAs array covering the range of 1100 to 1900 nm. A main purpose of the spectrometer is wavelength separation and detection. Variations in the grating/detector system are readily understood by those skilled in the art.

In an alternative embodiment, a broadband source is combined with a detector array without the use of a dispersive element. In one case, filters are placed in from the detectors. One type of filter are thin dielectric films, such as in Fabry-Perot interference filters. These filters may be placed into a linear, bundle, or rectangular pattern depending upon how the light is coupled to the detector. For example, a slit may be used in conjunction with a rectangular array of filters and detectors. Alternatively, a fiber may be used in conjunction with a bundle of filters and associated detectors. Another type of filter is a linear variable filter. For example, a linear variable filter may sit in from of a linear array of filters. Many variations on these optical layouts are known to those skilled in the art.

The Power/Control Module may be coupled to the user's belt or other location other than the measurement site. In an alternate embodiment the patient interface module contains a battery and two-way wireless communication system. In this configuration the Control/Power module may be carried by the patient. For example, a handheld computer or Palm computing platform can be equipped with a two-way wireless communication system for receiving data from the patient interface module and sending instructions. The computer system then provides the system with analysis capabilities.

In an alternate embodiment the base module contains a battery and two-way wireless communication system. In this configuration the Control/Power module is contained a remote location that is either carried by the patient or not. For example, a handheld computer or Palm computing platform can be equipped with a two-way wireless communication system for receiving data from the patient interface module and sending instructions. The computer system then provides the system with analysis capabilities.

The Control/Power Module contains the control electronics, power system, batteries, embedded computer and interface electronics. Control electronics provide a means for initiating events from the embedded or attached computer system and interfacing the detector electronics (amplifiers) which provide a voltage that is related to the detected light intensity. Digitizing the detected voltage through the use of an analog-to-digital converter is performed. The signals detected are used to form a spectrum which is represents the diffusely reflected and detected light intensity versus wavelength. In addition, historical measurements are made available through a display and/or an external communication port to a computer or computer system, e.g. a Palmtop. In an alternate embodiment, the measurement and ancillary information is transferred to a remote display and receiving unit, such as a handheld computer or stand-alone display module through a wireless communication. In this latter system, a display and receiving unit may be incorporated into a watch, pen, personal desktop assistance, cell phone, or blood glucose monitoring device.

Spectrometer

It is here noted, that variation of one component may affect optimal or preferred characteristics of other components. For example, variation in the source may affect the quality or design of the reflector, the thickness of the filter, the used aperture size, the time or power requirements for maintaining or heating the skin and/or fluorinert, and the diameter of the collection fiber. Similarly, changing another component such as the collection fiber diameter impacts the other elements. Those skilled in the art will appreciate the interaction of these elements. Those skilled in the art will also immediately appreciate that one or more components of the spectrometer may be changed without altering the scope of the invention.

Important regions to detect are permutations and combinations of bands due to water centered about 1450, 1900, or 2600 nm, protein bands centered about 1180, 1280, 1690, 1730, 2170, or 2285 nm, fat bands centered about 1210, 1675, 1715, 1760, 2130, 2250, or 2320 nm, or glucose bands centered about 1590, 1730, 2150, and 2272 nm.

A preferred physical orientation of the spectrometer is in a vertical position. For example, when sampling on the dorsal aspect of the forearm when the palm is face down on a support it is preferable for the sampling module to come down onto the arm from above. This allows the weight of the sampling module to be reproducible.

Standards

Near-infrared devices are composed of optical and mechanical components that vary due to manufacturing tolerances, vary in optical alignment, and change with time due to mechanical factors such as wear and strain, and environmental factors such as temperature variation. This results in changes in the x-axis of a given spectrometer with time as well as instrument-to-instrument variation. When a calibration model is used to extract information about a sample, such as the glucose concentration in the body, these instrument related changes result in wavelength uncertainty that reduces the accessibility of the signal related to the property of interest. These variations also degrades the device accuracy when a calibration model is transferred from one instrument to another.

A system for standardizing the wavelength axis of near-IR optical systems that measures light at a multiplicity of wavelengths is described in this section. The preferred embodiment is that presented in FIG. 2. The system described in this section may be used with the instrument configurations described in the remainder of this document. The spectrometer system detects the transmitted or reflected near-infrared infrared radiation from the sample within a specified wavelength range and the analyzer determines the absorbance at various wavelengths after a standardization procedure. Methods for standardizing the x-axis of a spectrometer based system rely on a comparative analysis of a master and slave spectra of a standardization material. A material with absorption bands in the targeted wavelength region is used for determining the x-axis. Typically, the reference or standard absorbance bands are reasonably sharp, stable, and distributed across the wavelength region of interest (1100 to 1900 nm). Common materials for this purpose are polystyrene, erbium oxide, dysprosium oxide, and holmium oxide though a large number of plastics may be used. Internal polystyrene has been used as a reference in the FOSS, formerly NIRSystems spectrometers. However, in these systems, polystyrene is used in conjunction with an actuated rotating grating and a single detector. In the preferred embodiment of this invention no actuated grating is used.

The material used for standardization may be measured external to the spectrometer system with an external mounting system. However, the material mounted in a separate standard mounting system external to the spectrometer must be placed on the device by the user at designated time periods. This process is subject to positioning error and increases the complexity of the measurement protocol from the standpoint of the user. This is particularly a problem in consumer oriented devices, such as non-invasive glucose sensors, in which the user may not be technically oriented.

Alternatively, the reference may be continuously mounted internal to the instrument in a separate light path. In this configuration, the internal wavelength standard may be measured simultaneously with the sample. Alternatively, the reference may be moved through an actuator into the main optical train at an appropriate time, optionally in an automated process. In either of these systems, the reference spectrum may be collected in transmittance of reflectance mode. However, it is preferable to collected an external reference in diffuse reflectance mode. For example a polystyrene disk placed at an angle to the incident light to minimize specular reflectance may be backed by a reflector such as a Labsphere® reference. For an internal reference, a similar arrangement may be used, but a transmittance spectrum is preferred.

The wavelength standardization system includes associated methods for measurement of a reference spectrum and a (wavelength) standardization spectrum through the spectroscopic measurement of a non-absorbing material and a material with known and immutable spectral absorbance bands respectively. The spectrum of the standardization material is used in-conjunction with an associated method for standardizing the x-axis of sample spectra that are collected subsequently. The method includes a master spectrum of the standardization material and a method for determining the discrepancy between the master and instrument standardization spectrum. The master spectrum and the wavelength regions are stored in nonvolatile memory of the instrument computer system. One method of calculating the phase difference or x-axis shift between the master and slave spectra is through the use of cross correlation. For example, one or more windows across the spectrum the x-axis phase shift between the master and acquired spectrum are determined through a cross-correlation function after removing instrument related baseline variations. The phase shift is used to correct (standardize) the x-axis of the acquired spectrum to the master spectrum. Other approaches include interpolation or wavelet transformation.

Preprocessing

After conversion of the photons into intensity and optionally absorbance units, preprocessing occurs. The detected spectrum may be processed through multiple preprocessing steps including outlier analysis, standardization, absorbance calculation, filtering, correction, and application to a linear or nonlinear model for generation of an estimate (measurement) of the targeted analyte or constituent which is displayed to the user.

Of particular note is the preprocessing step of bias correcting the spectral data collected in one or both of the X (spectra) and Y (glucose concentration) data. In particular, the first scan of a day may have a reference glucose concentration associated with it. This glucose concentration may be used as a bias correction for glucose determinations collected until subsequent calibration. Similarly, the first spectrum of the day may be used to adjust calibration components from the X block. Notably, the guide allows the same sampling location to be obtained until the guide is removed. This directly impacts the use of the first spectrum and reference glucose concentration to adjust the model in terms of preprocessing and subsequent model application.

Additional preprocessing techniques are covered in the introductory section. These techniques are well understood by those skilled in the art.

Modeling

Subsequent data analysis may include a soft model or a calibration such as PCR or PLS. Many other modes of data analysis exist such as neural networks. A method has been invented for calibrating the device to an individual or a group of individuals based upon a calibration data set. The calibration data set is comprised of paired data points of processed spectral measurements and reference biological parameter values. For example, in the case of glucose measurement, the reference values are one or more of the following: finger capillary blood glucose, alternate site capillary blood glucose, i.e. a site on the body other than the finger, interstitial glucose or venous blood glucose. The calibration data is subject to optimal sample selection to remove outliers, data correlating to ancillary factors and data with excessive variation. Spectral measurements are preprocessed prior to calibration through filtering and scattering correction and normalized to a background template collected each time the guide system is attached to the skin tissue. Measurements are performed after preprocessing data collected subsequent to calibration as discussed above through the calibration or model to measure the variation of the biological parameter relative to its value at the time the guide was attached. The scope of these techniques was addressed in the prior art section and are well known to those skilled in the art.

Figure 7:
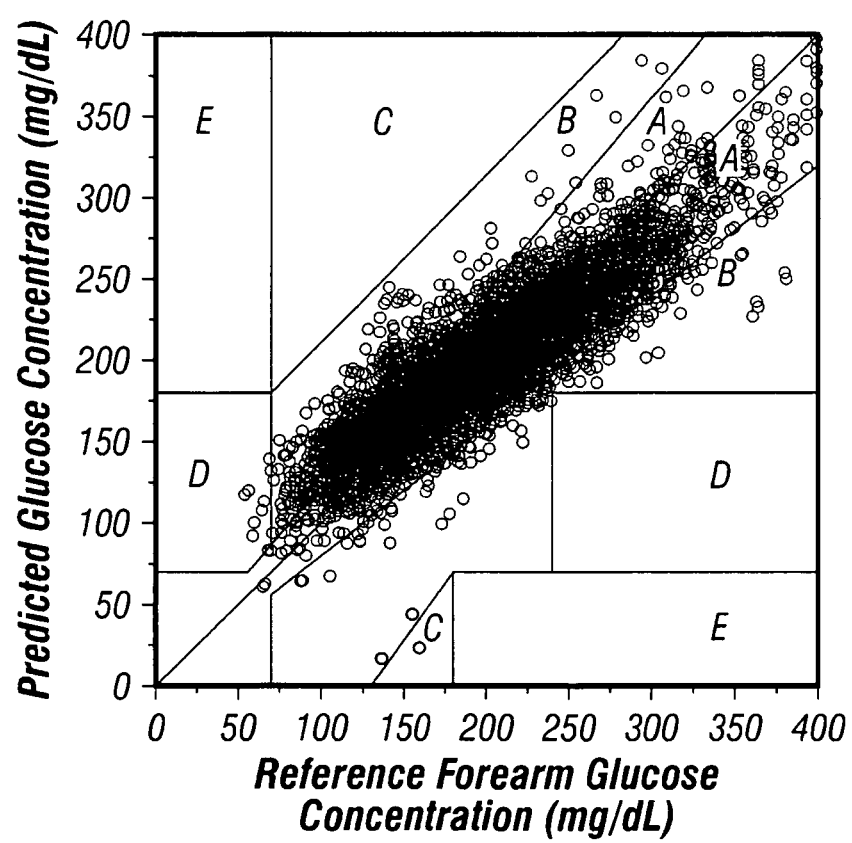
FIG. 7 shows noninvasive glucose predictions in a concentration correlation plot.

Results of a study using a noninvasive glucose analyzer are presented here. The study used a custom built noninvasive near-IR glucose analyzer. The analyzer is conceptually as presented in the preferred embodiment with components including a tungsten halogen source, a back-reflector, a bandpass optical filter, a fiber optic illumination bundle, a guide, a fluorinert coupling fluid, a guide, an aperture, a forearm sampling site, a collection fiber, a slit, a dispersive grating, and an InGaAs array detector though the spectrometer was larger in overall dimensions than in the preferred embodiment. However, the miniaturized sampling module has been demonstrated to deliver equivalent energy to the sample site. A calibration model was built. A subsequent prediction data set was initiated two weeks after all parameters were fixed in the calibration model. Subsequent prediction data (spectra) were collected with two spectrometers on seven people over a period of seven weeks. Preprocessing included a Savitsky-Golay first derivative with 27 points and mean centering. A PLS model was applied with a fifteen factor model to the resulting data over a range of 1200 to 1800 nm. A total of 976 glucose determinations were made. The outlier analysis program was automated. The results are presented in FIG. 7 in a concentration correlation plot overlaid with a Clarke error grid. Overall, 99.9% of the glucose predictions fell into the 'A' or 'B' region of the Clarke error grid. These glucose predictions are considered clinically accurate.

Docking Station

In the preferred embodiment, the base module is integrally connected to the docking station. In addition to the grating, detector assembly, and power supply, the docking station includes a computer and a glucose management center. The glucose management system may keep track of events occurring in time such as glucose intake, insulin delivery, and determined glucose concentration. These may be graphed with time or exported to exterior devices, such as a doctor's computer.

A process is provided for estimating the precision of the measurement through a statistical analysis of repeated or successive measurements. A method is implemented for determining when the biological parameter is close to a preset level through a statistical estimate of the confidence limits of a future analyte prediction. The prediction is made through a simple slope, e.g. change in the biological parameter over the change in time, estimate based on an exponentially moving average and the confidence limits are based upon the estimate of precision. Alternately, the prediction is made through a standard time series analysis. An alarm is invoked if the associated present alarm level is within the confidence interval of a future biological parameter prediction. This process is used, for example, to detect the potential for hypoglycemia in diabetics in the near future, e.g. within 10-30 minutes. In addition, the process is used to detect potential outliers through a determination of the statistical consistency of a particular measurement with its expected value.

Continuous/Semi-Continuous Glucose Determination

Continuous or semi-continuous measurements may be taken when the sampling module is in contact with the sampling site. Measurements of a biological parameter that are made at short intervals relative to the change in the biological parameter such that the measurement process is continuous. In the preferred embodiment, measurements may be made every six seconds. Realistically, the glucose concentration does not change to a measurable level within six seconds. Therefore, readings taken at a less frequent interval such as every 1, 5, 10, 20, 30, or 60 minutes can be made. Readings taken at this interval are still referred to as continuous and/or semi-continuous. The continuous readings may be performed in an automated fashion.

It is noted that when the biological parameter is slowly varying, the guide can remain attached to the individual while the rest of the system is intermittently attached at particular intervals to make continuous or semi-continuous readings.

An element of the invention is the use of the time based information and trends to perform other functions such as estimate of the precision, confidence intervals and prediction of future events.

A process is provided for estimating the precision of the measurement through a statistical analysis of repeated or successive measurements. A method is implemented for determining when the biological parameter is close to a preset level through a statistical estimate of the confidence limits of a future analyte prediction. The prediction is made through a simple slope, e.g. change in the biological parameter over the change in time, estimate based on an exponentially moving average and the confidence limits are based upon the estimate of precision. Alternately, the prediction is made through a standard time series analysis. An alarm is invoked if the associated present alarm level is within the confidence interval of a future biological parameter prediction. This process is used, for example, to detect the potential for hypoglycemia in diabetics in the near future, e.g. within 10-30 minutes. In addition, the process is used to detect potential outliers through a determination of the statistical consistency of a particular measurement with its expected value.

In circumstances in which the Control/Power module can be secured without disturbing the sample site the two modules are merged into one that are attached to the subject through the guide interface system. Finally, when the biological parameter is slowly varying, the guide can remain attached to the individual while the rest of the system is intermittently attached at particular intervals.

A link is disclosed to an insulin delivery system. When the monitored biological parameter is glucose, a link is provided to an insulin delivery system to provide a feedback mechanism for control purposes. The link is either a direct or a wireless connection. In addition, a communication system is provided for transmitting the patient's monitored glucose levels to his physician.

An Alternative Embodiments

As in the preferred embodiment, a primary alternative embodiment of the invention includes two main modules: a sampling module and base module connected though a communication bundle. The modules are as described in the preferred embodiment with the exception of the source and the associated wavelength selection/detection components. In the alternative embodiment of the invention, the spectrometer system uses LEDs to both provide near-infrared radiation to the sample and to perform wavelength selection over predefined wavelength ranges. This embodiment has the significant advantage of not requiring a dispersive element or interferometer based system for the purpose of wavelength selection. Rather, each LED provides near-infrared radiation over a band of wavelengths and thereby gives the necessary means for wavelength selection.

The wavelengths of the LEDs are selected specifically to optimize the signal-to-noise ratio of the net analyte signal of the target analyte and are arranged at various distances with respect to the detection elements to provide a means for sampling various tissue volumes for the purpose of averaging and the determination of a differential measurement. The LEDs are sequentially energized one at a time and/or in groups to obtain various estimates of the diffuse reflectance of various tissue volumes at specific wavelengths or bands of wavelengths. In addition, the LEDs can be pulsed to provide short measurements with high signal-to-noise ratios. This provides greater illumination intensity, while avoiding photo heating of the sampled tissue volume. Alternately, the LEDs can be modulated at a particular duty cycle and frequency to provide a means for removing additive noise and simultaneous measurement of multiple wavelengths.

The wavelengths of the LED(s) are selected specifically to optimize the signal-to-noise ratio of the net analyte signal of the target biological parameter and are arranged at various distances with respect to the detection elements to provide a means for sampling various tissue volumes for the purpose of averaging and the determination of a differential measurement. The LEDs are sequentially energized one at a time and/or in groups to obtain various estimates of the diffuse reflectance of various tissue volumes. In addition, the LEDs can be pulsed to provided short measurements with a high signal-to-noise ratio while avoiding photo heating of the sampled tissue volume. Alternately, the LEDs can be modulated at a particular duty cycle and frequency to provide a means for removing additive noise and simultaneous measurement of multiple wavelengths.

With an LED source, the remainder of the spectrometer remains as in the preferred embodiment and its species. For example, the LED's may be stabilized with control electronics, optics may be used to guide the source intensity to the sampled aperture, a guide may be used, a coupling fluid may be used, temperature stabilization of the source and or sample may be used, collection optics integrate with the sampled skin directly, a communication bundle may be employed, and a base module is used with or without a docking station. As in the preferred embodiment, the detector may stare directly at the tissue.

Embodiments

A number of instrument configurations of the alternative embodiment are presented below. Those skilled in the art will recognize that permutations and combinations of these embodiments are possible.

In the simplest embodiment, the LEDs may illuminate the sample directly, as in FIG. 8. In FIG. 8, a coupling fluid 84, as disclosed above, is shown provides between the device and the tissue sample. An optional mixing chamber with a reflective surface may be used between the LEDs 80 and the optical window 81 to provide a nearly uniform distribution onto the tissue region 82 surrounding the detection fiber 83. A spacer 85 may also be provided between the fiber and the LEDs. In this embodiment, the LEDs are designed with a bandwidth enabling the measurement, and the LEDs are arranged in a manner that allows the sampling and detection of a particular tissue volume at a particular band of wavelengths. Each LED may be recessed into a material 91 having a reflective surface 90 as shown in FIG. 9.

In this scenario, two arrangements are used. First, a mixing chamber is present as shown in FIG. 8 with the filter inserted in the place of the optical window. This allows the LED's to be used in much the same way as a broadband source.

Second, the illumination-to-detection distance may be used for measurement purposes so the mixing chamber is removed and the LEDs are put in close proximity or even touching the overall sampling site via optional filters. In this second mode, the distance from the illumination spot of the LED to the collection optics is known. This allows the average depth of penetration of the photons and average pathlength to be known. This allows wavelength dependent scanning of depth and radial variation from the collection spot, and allows wavelength specific information to be used in an indirect reading of the glucose concentration.

In the preferred embodiment, groups of LEDs (FIG. 10; 100) are employed with each group associated with a single filter type, more than one physical filter may be necessary. The LEDs are arranged at distances surrounding the detection fiber and energized according to a strategy enabling the detection of light associated with different wavelength bands and different illumination to detection distances (see FIG. 10). In one embodiment (FIG. 10a) the groups of LEDs are arranged in annuli (rings) at specific distances surrounding the detection fiber. The filters are arranged in rings surrounding the detection fiber and covering the associated LEDs. Each annular ring of the filter may have its own filter characteristics. In a second arrangement (FIG. 10b), groups of LEDs are arranged in wedges surrounding the detection fiber. In the second embodiment the filters may be of a wedged or triangular shape and are arranged to cover their associated LEDs. Each wedge filter may have its own filter characteristics.

In another embodiment, each LED or group of LEDs has an associated optical filter that is used to limit the bandwidth of emitted light. A different filter is mounted such that the light emitted and delivered to the sample from the LED passes through the filter. The filter associated with an LED is designed with a specific bandwidth and is centered on a particular wavelength that is within the native bandwidth of the LED. To provide for a broader illumination pattern or to increase the light energy delivered to the sample, groups of LEDs can be associated with the same filter. Through alternate energization of the LEDs or by modulating each LED or LED group at different frequencies (and demodulating after detection), narrow wavelength bands on the order of 5-100 nm can be distinguished and measured through a single element detector.

In another embodiment, the LEDs have a bandwidth relatively broader than the net analyte and interference signals. The light collected by the detection fiber is passed through a slit and imaged onto dispersive element which disperses the band of detected light onto an array of detector elements. In this configuration, optical filters on the LEDs are not employed.

In another embodiment, the LED's are used in a spectrometer without a dispersive element and a single element detector. In one case, thin dielectric films are used as in Fabry-Perot interference filters. A filter is associated with each LED. In a second case, an interferometer composed of two parallel, highly reflecting plates separated by an air gap may be used. One of the parallel plates may be translated mechanically such that the distance between the plates varies. Technically, this is a Fabry-Perot interferometer. When the mirror distance is fixed and adjusted for parallelism by a spacer such as invar or quartz, the system is referred to as a Fabry-Perot etalon. Both cases allow narrow excitation lines and may be used by sequentially firing the LED's as above.

A number of spectrometer configurations are possible for this measurement as are outlined above. Basically the spectroscopic measurement system includes a source of near-infrared radiation, a wavelength selection system, an interface to the patient, photon guiding optics, and a detector.

Although the invention has been described herein with reference to certain preferred embodiments, one skilled in the art will readily appreciate that other applications may be substituted for those set forth herein without departing from the spirit and scope of the present invention. Accordingly, the invention should only be limited by the claims included below.

The invention claimed is:

1. An apparatus for noninvasive measurement of glucose at a sample site through near-infrared spectroscopy, comprising:
    a base module comprising a grating and a detector array;
    a sample module configured to securely and removeably interface to the sample site, said sample module coupled to said base module, said sample module comprising:
    an illumination source;
    a first optic configured to be located between said illumination source and the sample site, wherein said first optic removes heat; and
    a second optic configured to be located between said illumination source and the sample site, wherein said second optic contacts an area about the sample site and aids in mechanical stabilization of a collection optic, said collection optic configured to be in close proximity to the sample site, wherein said close proximity reduces specular reflectance; and
    a communication bundle for carrying optical and/or electrical signals between said base module and said sample module, and for carrying power to said sample module from said base module.

2. The apparatus of claim 1, said sample module further comprising at least one of:
    a low profile sample interface;
    a low wattage stabilized source in close proximity to said sampled site;
    an excitation collection cavity or optics;
    a guide;
    a preheated interfacing solution;
    means for maintaining a temperature controlled skin sample;
    a mechanism for constant pressure and/or displacement of sampled skin tissue; and
    a photonic stimulation source.

3. The apparatus of claim 1, said sample module further comprising:
    a guide configured to securely and removeably attach to the sample site, said guide configured to continuously and/or periodically physically and optically locate said sample module relative to the sample site in a repeatable manner and with minimal disturbance to the sample site.

4. The apparatus of claim 3, further comprising means for:
    pretreatment of said sample site sample module;
    reduction of specular reflectance;
    to approach and maintain appropriate sample site temperature variation; and
    minimizing sample site hydration changes.

5. The apparatus of claim 3, wherein said sample module reversibly couples into said guide for reproducible contact pressure and/or sample location.

6. The apparatus of claim 5, said guide further comprising:
    at least one magnet for aiding in positioning a sample module probe to ensure proper penetration of said probe into a guide aperture, and to enable a constant pressure and/or displacement interface of said sample site; wherein said magnet is optionally electrically activated to facilitate controlled movement into a guide aperture and to allow, through reversal of said magnet poles, withdrawal from said guide aperture without pulling.

7. The apparatus of claim 1, wherein said sample module and said base module are integrated together into a handheld unit.

8. The apparatus of claim 1, further comprising:
    a photodiode; and
    a feedback controller for allowing said illumination source to be driven at different levels at different points in time during and prior to data acquisition,
    wherein said photodiode is placed before an order sorter to detect visible light from said illumination source.

9. The apparatus of claim 1, said communication bundle further comprising:
    quick connect optics which comprise:
    a first collection optic that is fixed into said communication bundle; and
    a connector in said communication bundle for accepting a connection to said sample module.

10. The apparatus of claim 1, wherein said first optic comprises:
    a silicon filter for removing light under 1050 nm, wherein a grating is used in the 1150 to 1850 nm region without detection of second or higher order light off of said grating,
    wherein said silicon filter is placed before the grating.

11. The apparatus of claim 1, said sample module comprising:
    a surface defining an aperture for providing optical pathlengths within a sample for indirectly monitoring glucose concentrations within a body, providing acceptable energy delivery to said sample site, and providing appropriate heating/temperature control of said sample site.

12. The apparatus of claim 11, further comprising:
  means for performing an indirect determination of glucose from sample constituents which comprise any of: fat, protein, and water, wherein said sample constituents are distributed as a function of depth in a sample, wherein a magnitude of an indirect signal varies with said aperture.

13. The apparatus of claim 1, sample module further comprising means for treating said sample site with any of:
  photonic stimulation;
  ultrasound pretreatment;
  mechanical stimulation;
  cooling; and
  heating.

14. The apparatus of claim 1, said sample module further comprising:
  a light emitting diode for providing photonic stimulation to induce capillary blood vessel dilation.

15. The apparatus of claim 1, further comprising:
  means for using any of a signal and an absence of observed intensity at large water absorbance bands about 1450, 1900, and 2500 nm to determine when said sample module is in close proximity with a sample site surface.

16. The apparatus of claim 1, wherein said base module further comprises:
  a two-way wireless communication system for transferring data between said sample module and any of said base module and a data collection/processing system.

17. The apparatus of claim 1, wherein said base module is integrally connected to a docking station, wherein said docking station comprises a computer and a glucose management center; wherein said glucose management center keeps track of events occurring in time comprising any of glucose intake, insulin delivery, and determined glucose concentration.

18. The apparatus of claim 1, further comprising:
  means for taking any of continuous and semi-continuous measurements when said sample module is in proximate contact with said sample site.

19. The apparatus of claim 1, said sample module further comprising:
  a spectrometer system comprising light emitting diodes to provide near-infrared radiation to said sample site over predefined wavelength ranges, wherein each of said light emitting diodes provides near-infrared radiation over a band of wavelengths.

* * * * *